(12) United States Patent
Narendranath et al.

(10) Patent No.: US 8,815,552 B2
(45) Date of Patent: *Aug. 26, 2014

(54) SYSTEM FOR FERMENTATION OF BIOMASS FOR THE PRODUCTION OF ETHANOL

(75) Inventors: Neelakantam V. Narendranath, Sioux Falls, SD (US); David Charles Carlson, Yankton, SD (US)

(73) Assignee: Poet Research, Inc., Sioux Falls, SD (US)

( * ) Notice: Subject to any disclaimer, the term of this patent is extended or adjusted under 35 U.S.C. 154(b) by 360 days.

This patent is subject to a terminal disclaimer.

(21) Appl. No.: 12/717,015

(22) Filed: Mar. 3, 2010

(65) Prior Publication Data

US 2010/0227369 A1  Sep. 9, 2010

Related U.S. Application Data

(60) Provisional application No. 61/157,140, filed on Mar. 3, 2009, provisional application No. 61/157,142, filed on Mar. 3, 2009, provisional application No. 61/157,137, filed on Mar. 3, 2009.

(51) Int. Cl.
*C12P 7/06* (2006.01)
*C12P 7/10* (2006.01)
*C12M 1/00* (2006.01)
*C12M 1/33* (2006.01)

(52) U.S. Cl.
CPC *C12P 7/10* (2013.01); *C12M 45/04* (2013.01); *C12M 23/58* (2013.01); *C12M 45/02* (2013.01); *C12M 21/12* (2013.01); *C12M 43/02* (2013.01); *Y02E 50/16* (2013.01)
USPC ........................................................ 435/161

(58) Field of Classification Search
USPC ........................................................ 435/161
See application file for complete search history.

(56) References Cited

U.S. PATENT DOCUMENTS

| | | |
|---|---|---|
| 2,440,925 A | 5/1948 | Boeckeler |
| 3,212,932 A | 10/1965 | Hess et al. |
| 3,940,492 A | 2/1976 | Ehnstrom |
| 4,009,074 A | 2/1977 | Walon |
| 4,014,743 A | 3/1977 | Black |
| 4,029,515 A | 6/1977 | Kiminki et al. |
| 4,092,434 A | 5/1978 | Yoshizumi et al. |
| 4,152,197 A | 5/1979 | Lindahl et al. |
| 4,168,988 A | 9/1979 | Riehm et al. |
| 4,243,750 A | 1/1981 | Muller et al. |
| 4,279,747 A | 7/1981 | Chen |
| 4,287,303 A | 9/1981 | Dahlberg et al. |
| 4,309,254 A | 1/1982 | Dahlstrom et al. |
| 4,316,956 A | 2/1982 | Lutzen |
| 4,342,831 A | 8/1982 | Faber et al. |
| 4,358,536 A | 11/1982 | Thorsson et al. |
| 4,361,651 A | 11/1982 | Keim |
| 4,376,163 A | 3/1983 | Ehnstrom |
| 4,425,433 A | 1/1984 | Neves |
| 4,427,453 A | 1/1984 | Reitter |
| 4,432,805 A | 2/1984 | Nuuttila et al. |
| 4,460,687 A | 7/1984 | Ehnstrom |
| 4,461,648 A | 7/1984 | Foody |
| 4,474,883 A | 10/1984 | Yamamoto et al. |
| 4,490,469 A | 12/1984 | Kirby et al. |
| 4,514,496 A | 4/1985 | Yoshizumi et al. |
| 4,522,920 A | 6/1985 | Thorsson et al. |
| 4,529,699 A | 7/1985 | Gerez et al. |
| 4,530,846 A | 7/1985 | Nagodawithana et al. |
| 4,540,663 A | 9/1985 | Witt |
| 4,552,616 A | 11/1985 | Kauppi |
| 4,591,560 A | 5/1986 | Kainuma et al. |
| 4,612,286 A | 9/1986 | Sherman et al. |
| 4,618,579 A | 10/1986 | Dwiggins et al. |
| 4,668,340 A | 5/1987 | Sherman |
| 4,716,218 A | 12/1987 | Chen et al. |
| 4,727,026 A | 2/1988 | Sawada et al. |
| 4,752,579 A | 6/1988 | Arena et al. |
| 4,760,025 A | 7/1988 | Estell et al. |
| 4,863,864 A | 9/1989 | Ashikari et al. |

(Continued)

FOREIGN PATENT DOCUMENTS

| | | |
|---|---|---|
| CA | 1143677 | 3/1983 |
| DE | 267508 | 5/1989 |

(Continued)

OTHER PUBLICATIONS

Taherzadeh et al., Int. J. Mol. Sci., 9(9), 1621-1651, 2008.*
De Mancilha et al., "Evaluation of Ion Exchange Resins for Removal of Inhibitory Compounds from Corn Stover Hydrolyzate for Xylitol Fermentation", Biotechnology Progress, 2003, vol. 19, pp. 1837-1841.
Gulati et al., "Assessment of Ethanol Production Options for Corn Products", Bioresource Technology, 1996, vol. 58, pp. 253-264.
Jeffries et al., "Fermentation of Hemicellulosic Sugars and Sugar Mixtures by Candida shehatae", Biotechnology and Bioengineering, 1988, vol. 31, pp. 502-506.
Nigam et al., "Enzyme and microbial systems involved in starch processing", Enzyme and Microbial Technology, 1995, vol. 17, pp. 770-778.

(Continued)

*Primary Examiner* — Maryam Monshipouri
(74) *Attorney, Agent, or Firm* — Kagan Binder, PLLC

(57) ABSTRACT

A biorefinery and a system for producing a fermentation product from biomass are disclosed. The biorefinery comprises a preparation system to prepare the biomass into prepared biomass; a pre-treatment system to pre-treat the prepared biomass with a dilute acid for separation into a first component from which pentose can accessed for fermentation and a second component from which hexose can be made available for fermentation; a first treatment system to treat the first component into a treated first component by removing removed components from the first component; a first fermentation system to produce a first fermentation product from the pentose; a distillation system to recover ethanol from the first fermentation product; and a treatment system to process removed components. The biomass comprises lignocellulosic material, which comprises at least one of corn cobs, corn plant husks, corn plant leaves and corn plant stalks.

16 Claims, 18 Drawing Sheets

(56) References Cited

U.S. PATENT DOCUMENTS

| | | |
|---|---|---|
| 4,876,196 A | 10/1989 | Salzbrunn et al. |
| 4,908,098 A | 3/1990 | DeLong et al. |
| 4,933,279 A | 6/1990 | Carroll et al. |
| 4,941,944 A | 7/1990 | Chang |
| 4,997,488 A | 3/1991 | Gould et al. |
| 5,061,497 A | 10/1991 | Thacker et al. |
| 5,084,385 A | 1/1992 | Ashikari et al. |
| 5,087,417 A | 2/1992 | Dumbroff et al. |
| 5,125,977 A | 6/1992 | Grohmann et al. |
| 5,171,592 A | 12/1992 | Holtzapple et al. |
| 5,177,008 A | 1/1993 | Kampen |
| 5,177,009 A | 1/1993 | Kampen |
| 5,180,669 A | 1/1993 | Antrim |
| 5,221,357 A | 6/1993 | Brink |
| 5,231,017 A | 7/1993 | Lantero et al. |
| 5,250,182 A | 10/1993 | Bento et al. |
| 5,260,089 A | 11/1993 | Thornberg |
| RE34,606 E | 5/1994 | Estell et al. |
| 5,322,778 A | 6/1994 | Antrim et al. |
| 5,328,562 A | 7/1994 | Rafferty et al. |
| 5,338,366 A | 8/1994 | Grace et al. |
| 5,364,770 A | 11/1994 | Berka et al. |
| 5,366,558 A | 11/1994 | Brink |
| 5,370,999 A | 12/1994 | Stuart |
| 5,411,594 A | 5/1995 | Brelsford |
| 5,424,417 A | 6/1995 | Torget et al. |
| 5,498,766 A | 3/1996 | Stuart et al. |
| 5,536,325 A | 7/1996 | Brink |
| 5,545,543 A | 8/1996 | Zinnamosca et al. |
| 5,559,031 A | 9/1996 | Zinnamosca et al. |
| 5,562,777 A | 10/1996 | Farone et al. |
| 5,580,389 A | 12/1996 | Farone et al. |
| 5,597,714 A | 1/1997 | Farone et al. |
| 5,628,830 A | 5/1997 | Brink |
| 5,652,127 A | 7/1997 | Mitchinson et al. |
| 5,688,674 A | 11/1997 | Choi et al. |
| 5,693,296 A | 12/1997 | Holtzapple et al. |
| 5,705,369 A | 1/1998 | Torget et al. |
| 5,711,817 A | 1/1998 | Titmas |
| 5,721,127 A | 2/1998 | Deweer et al. |
| 5,721,128 A | 2/1998 | Deweer et al. |
| 5,726,046 A | 3/1998 | Farone et al. |
| 5,733,758 A | 3/1998 | Nguyen |
| 5,736,375 A | 4/1998 | Deweer et al. |
| 5,736,499 A | 4/1998 | Mitchinson et al. |
| 5,756,714 A | 5/1998 | Antrim et al. |
| 5,769,934 A | 6/1998 | Ha et al. |
| 5,782,982 A | 7/1998 | Farone et al. |
| 5,817,498 A | 10/1998 | Deweer et al. |
| 5,820,687 A | 10/1998 | Farone et al. |
| 5,824,532 A | 10/1998 | Barnett et al. |
| 5,849,549 A | 12/1998 | Barnett et al. |
| 5,865,898 A | 2/1999 | Holtzapple et al. |
| 5,879,463 A | 3/1999 | Proenca |
| 5,916,780 A | 6/1999 | Foody et al. |
| 5,932,452 A | 8/1999 | Mustranta et al. |
| 5,932,456 A | 8/1999 | Van Draanen et al. |
| 5,958,739 A | 9/1999 | Mitchinson et al. |
| 5,972,118 A | 10/1999 | Hester et al. |
| 5,975,439 A | 11/1999 | Chieffalo et al. |
| 5,981,237 A | 11/1999 | Meagher et al. |
| 6,022,419 A | 2/2000 | Torget et al. |
| 6,074,854 A | 6/2000 | Deweer et al. |
| 6,090,595 A | 7/2000 | Foody et al. |
| 6,136,576 A | 10/2000 | Diaz-Torres et al. |
| 6,171,817 B1 | 1/2001 | Berka et al. |
| 6,228,177 B1 | 5/2001 | Torget |
| 6,313,328 B1 | 11/2001 | Ulrich et al. |
| 6,379,504 B1 | 4/2002 | Miele et al. |
| 6,419,788 B1 | 7/2002 | Wingerson |
| 6,423,145 B1 | 7/2002 | Nguyen et al. |
| 6,451,063 B1 | 9/2002 | Clarkson et al. |
| 6,509,180 B1 | 1/2003 | Verser et al. |
| 6,538,182 B1 | 3/2003 | Thompson et al. |
| 6,555,350 B2 | 4/2003 | Ahring et al. |
| 6,616,948 B2 | 9/2003 | Gustavsson et al. |
| 6,620,292 B2 | 9/2003 | Wingerson |
| 6,660,506 B2 | 12/2003 | Nguyen et al. |
| 6,664,095 B1 | 12/2003 | Suryanarayan et al. |
| 6,692,578 B2 | 2/2004 | Schmidt et al. |
| 6,709,527 B1 | 3/2004 | Fechter et al. |
| 6,770,168 B1 | 8/2004 | Stigsson |
| 6,774,284 B1 | 8/2004 | Thompson et al. |
| 6,803,218 B1 | 10/2004 | Seyfried et al. |
| 6,849,439 B2 | 2/2005 | Henson et al. |
| 6,849,782 B2 | 2/2005 | Thompson et al. |
| 6,855,529 B2 | 2/2005 | Thompson et al. |
| 6,867,237 B1 | 3/2005 | Taylor et al. |
| 6,878,860 B1 | 4/2005 | Thompson et al. |
| 7,198,925 B2 | 4/2007 | Foody |
| 7,238,242 B2 | 7/2007 | Pinatti et al. |
| 7,344,876 B2 | 3/2008 | Levine |
| 7,354,743 B2 | 4/2008 | Vlasenko et al. |
| 7,455,997 B2 | 11/2008 | Hughes |
| 7,501,025 B2 | 3/2009 | Bakker et al. |
| 7,503,981 B2 | 3/2009 | Wyman et al. |
| 7,579,177 B2 | 8/2009 | Olsen et al. |
| 7,585,652 B2 | 9/2009 | Foody et al. |
| 7,604,967 B2 | 10/2009 | Yang et al. |
| 7,622,284 B2 | 11/2009 | Op Den Camp et al. |
| 7,649,086 B2 | 1/2010 | Belanger et al. |
| 7,666,637 B2 | 2/2010 | Nguyen |
| 7,670,813 B2 | 3/2010 | Foody et al. |
| 7,709,042 B2 | 5/2010 | Foody et al. |
| 7,754,456 B2 | 7/2010 | Penttila et al. |
| 7,754,457 B2 | 7/2010 | Foody et al. |
| 7,807,419 B2 | 10/2010 | Hennessey et al. |
| 7,815,741 B2 | 10/2010 | Olson |
| 7,815,876 B2 | 10/2010 | Olson |
| 7,819,976 B2 | 10/2010 | Friend et al. |
| 7,875,444 B2 | 1/2011 | Yang et al. |
| 7,901,511 B2 | 3/2011 | Griffin et al. |
| 7,919,291 B2 | 4/2011 | Lewis et al. |
| 8,057,639 B2 | 11/2011 | Pschorn et al. |
| 8,057,641 B2 | 11/2011 | Bartek et al. |
| 8,123,864 B2 | 2/2012 | Christensen et al. |
| 8,288,600 B2 | 10/2012 | Bartek et al. |
| 8,450,094 B1 | 5/2013 | Narendranath et al. |
| 2002/0192774 A1 | 12/2002 | Ahring et al. |
| 2003/0134395 A1 | 7/2003 | Shetty et al. |
| 2003/0134396 A1 | 7/2003 | Shetty et al. |
| 2003/0180900 A1 | 9/2003 | Lanteo |
| 2003/0203454 A1 | 10/2003 | Chotani et al. |
| 2004/0023349 A1 | 2/2004 | Bisgaard-Frantzen et al. |
| 2004/0043117 A1 | 3/2004 | Cope et al. |
| 2004/0060673 A1 | 4/2004 | Phillips et al. |
| 2004/0063184 A1 | 4/2004 | Grichko |
| 2004/0080923 A1 | 4/2004 | Janisch |
| 2004/0091983 A1 | 5/2004 | Veit et al. |
| 2004/0115779 A1 | 6/2004 | Olsen et al. |
| 2004/0157301 A1 | 8/2004 | Chotani et al. |
| 2004/0192896 A1 | 9/2004 | Finch |
| 2004/0197409 A1 | 10/2004 | Iyer et al. |
| 2004/0219649 A1 | 11/2004 | Olsen et al. |
| 2004/0234649 A1 | 11/2004 | Lewis et al. |
| 2005/0026261 A1 | 2/2005 | Otto et al. |
| 2005/0042737 A1 | 2/2005 | Vikso-Nielsen et al. |
| 2005/0069998 A1 | 3/2005 | Ballesteros Perdices et al. |
| 2005/0100996 A1 | 5/2005 | Lantero, Jr. et al. |
| 2005/0136525 A1 | 6/2005 | Baldwin et al. |
| 2005/0208623 A1 | 9/2005 | Baldwin et al. |
| 2005/0233030 A1 | 10/2005 | Lewis et al. |
| 2005/0239181 A1 | 10/2005 | Lewis et al. |
| 2006/0051847 A1 | 3/2006 | Gunnarsson et al. |
| 2006/0246563 A1 | 11/2006 | Eroma et al. |
| 2006/0281157 A1 | 12/2006 | Chotani et al. |
| 2007/0178567 A1 | 8/2007 | Lewis |
| 2007/0196907 A1 | 8/2007 | Lewis |
| 2007/0202214 A1 | 8/2007 | Lewis et al. |
| 2008/0032373 A1 | 2/2008 | Bhargava |
| 2008/0277082 A1 | 11/2008 | Pschorn et al. |
| 2008/0295981 A1 | 12/2008 | Shin et al. |
| 2009/0053793 A1 | 2/2009 | Lefebvre et al. |
| 2009/0308383 A1 | 12/2009 | Shin et al. |

(56) References Cited

U.S. PATENT DOCUMENTS

| | | | |
|---|---|---|---|
| 2010/0003733 A1 | 1/2010 | Foody et al. | |
| 2010/0041116 A1 | 2/2010 | Lewis et al. | |
| 2010/0144001 A1 | 6/2010 | Horton | |
| 2010/0151549 A1 | 6/2010 | Bhargava | |
| 2010/0159552 A1 | 6/2010 | Benson et al. | |
| 2010/0196980 A1* | 8/2010 | Smith et al. | 435/161 |
| 2010/0227369 A1 | 9/2010 | Narendranath | |
| 2010/0233771 A1 | 9/2010 | McDonald | |
| 2010/0285553 A1 | 11/2010 | Delmas et al. | |
| 2011/0070618 A1 | 3/2011 | Lewis et al. | |
| 2011/0079219 A1 | 4/2011 | McDonald et al. | |
| 2011/0094505 A1 | 4/2011 | Bulla et al. | |
| 2011/0097446 A1 | 4/2011 | Lewis et al. | |
| 2011/0111085 A1 | 5/2011 | Lewis et al. | |
| 2011/0171708 A1 | 7/2011 | Larsen | |
| 2011/0250312 A1 | 10/2011 | Lewis | |
| 2011/0269202 A1 | 11/2011 | Taron et al. | |
| 2012/0129234 A1 | 5/2012 | McDonald et al. | |
| 2012/0138246 A1 | 6/2012 | Christensen et al. | |
| 2012/0201947 A1 | 8/2012 | Stuart | |
| 2012/0309069 A1 | 12/2012 | Bell et al. | |
| 2013/0065289 A1 | 3/2013 | Carlson | |
| 2013/0143290 A1 | 6/2013 | Narendranath | |
| 2013/0337521 A1 | 12/2013 | Carlson et al. | |
| 2014/0024826 A1 | 1/2014 | Narendranath et al. | |
| 2014/0065700 A1 | 3/2014 | Narendranath et al. | |

FOREIGN PATENT DOCUMENTS

| | | |
|---|---|---|
| EP | 0 044 658 | 1/1982 |
| EP | 0 098 490 | 1/1984 |
| EP | 0138428 | 4/1985 |
| EP | 0 140 410 | 5/1985 |
| EP | 0 159 795 | 10/1985 |
| EP | 0 171 218 | 2/1986 |
| EP | 0 884 391 | 12/1998 |
| EP | 1 259 466 | 11/2002 |
| FR | 2 397 486 | 2/1979 |
| FR | 2 609 046 | 7/1988 |
| GB | 2089836 | 12/1981 |
| JP | 58-005145 | 1/1983 |
| JP | 59-179093 | 10/1984 |
| RU | 2001103 | 10/1993 |
| RU | 2127760 | 3/1999 |
| WO | WO 91/03543 | 3/1991 |
| WO | WO-91/03543 A1 | 3/1991 |
| WO | WO 92/20777 | 11/1992 |
| WO | WO 94/08027 | 4/1994 |
| WO | WO 94/29475 | 12/1994 |
| WO | WO 95/08648 | 3/1995 |
| WO | WO 95/13362 | 5/1995 |
| WO | WO 97/27047 | 7/1997 |
| WO | WO 98/14270 | 4/1998 |
| WO | WO 98/56958 | 12/1998 |
| WO | WO 99/06133 | 2/1999 |
| WO | WO 00/14120 | 3/2000 |
| WO | WO 00/61858 | 10/2000 |
| WO | WO 00/73221 | 12/2000 |
| WO | WO 01/32715 | 5/2001 |
| WO | WO 01/60752 | 8/2001 |
| WO | WO 02/14598 | 2/2002 |
| WO | WO 02/24882 | 3/2002 |
| WO | WO 02/38786 | 5/2002 |
| WO | WO 02/38787 | 5/2002 |
| WO | WO 02/051561 | 7/2002 |
| WO | WO 02/067691 | 9/2002 |
| WO | WO 02/070753 | 9/2002 |
| WO | WO 02/074895 | 9/2002 |
| WO | WO 03/013714 | 2/2003 |
| WO | WO 03/018766 | 3/2003 |
| WO | WO 03/062430 | 7/2003 |
| WO | WO 03/066816 | 8/2003 |
| WO | WO 03/066826 | 8/2003 |
| WO | WO 03/068976 | 8/2003 |
| WO | WO 03/071025 | 8/2003 |
| WO | WO 03/078644 | 9/2003 |
| WO | WO-2004/080923 A2 | 9/2004 |
| WO | WO 2004/080923 A2 | 9/2004 |
| WO | WO 2004/081193 | 9/2004 |
| WO | WO 2004/106533 A1 | 12/2004 |
| WO | WO-2004/106533 A1 | 12/2004 |
| WO | WO 2005/052148 | 6/2005 |
| WO | WO 2005/082155 | 9/2005 |
| WO | WO 2005/099854 | 10/2005 |
| WO | WO 2006/032282 | 3/2006 |
| WO | WO 2006/034590 | 4/2006 |
| WO | WO 2006/056838 | 6/2006 |
| WO | WO 2007/009463 | 1/2007 |
| WO | WO 2008/095098 | 8/2008 |
| WO | WO 2008/131229 | 10/2008 |
| WO | 2008/144878 | * 12/2008 |
| WO | WO 2009/045651 | 4/2009 |
| WO | WO 2009/108773 | 9/2009 |
| WO | WO 2010/113129 | 10/2010 |
| WO | WO 2010/113130 | 10/2010 |
| WO | WO 2011/116317 | 9/2011 |
| WO | WO 2011/159915 | 12/2011 |
| WO | WO 2012/042497 | 4/2012 |
| WO | WO 2012/042498 | 4/2012 |
| WO | WO 2012/103281 | 8/2012 |
| WO | WO 2012/131665 | 10/2012 |

OTHER PUBLICATIONS

Nilvebrandt et al., "Detoxification of Lignocellulose Hydrolysates with Ion-Exchange Resins", Applied Biochemistry and Biotechnology, vols. 91-93, 2001, pp. 35-49.

U.S. Appl. No. 12/716,989, filed Mar. 3, 2010, Kwiatkowski.

Abouzied et al., "Direct fermentation of potato starch to ethanol by cocultures of *Aspergillus niger* and *Saccharomyces cerevisiae*", Appl Environ Microbiol, 1986, 52(5):1055-9.

Aden et al., "Lignocellulolsic biomass to ethanol process design and economics utilizing co-current dilute acid prehydrolysis and enzymatic hydrolysis for corn stover", NREL, NREL-TP-510-32438, 2002, pp. 1-88 and Appendices A-G.

Aldrich, "New enzymes lower ethanol production fuel costs", BridgeNews, Kansas City, 2004.

Allison et al., "Transformation of the thermophilic fungus humicola grisea var. thermoidea and overproduction of humicola glucoamylase", Curr Genet, 1992, 21:225-229.

Argus Leader.Com., Web Page—Business—Broin Goes to Court, Printed Jun. 27, 2006, pp. 1-3.

Ashikari et al., "rhizopus raw-starch-degrading glucoamylase: its cloning and expression in yeast", Agric. Bio. Chem., 1986, 50(4):957-964.

Bardini et al., "Continuous clarification of grape must by flotation," Vini d'italia, 1992, 34(1):31-38, Abstract.

Belya et al., "Composition of corn and distillers dried grains with solubles from dry grind ethanol processing", Bioresource Technology, 2004, 94:293-298.

Berven, "The Making of Broin Project", Ethanol Producer Magazine, Feb. 2005, pp. 66-71.

Biotimes: The enzyme e-zine, "Fuel Ethanol Products" (Jan. 2003).

Biswas et al., "Analysis of Headspace Compounds of Distillers Grains using SPME in Conjunction with GC/MS and TGA", Journal of Cereal Science, 2001, 33:223-229.

Boel et al., "Glucoamylases G1 and G2 from *Aspergillus niger* are synthesized from two different but closely related mRNAs", The EMBO Journal, 1984, 3(5):1097-1102.

Bothast, "Ethanol research facility one of a kind," Industrial Oil Products Article, 2004, 15(8):518-519.

Brown et al., "The effect of temperature on the ehtanol tolerance of the yeast, *Saccharomyces uvarum*", Biotechnology Letters, 1982, 4(4):269-274.

Bryan, "Changing the Game", Ethanol Producer Magazine, Aug. 2005, pp. 58-63.

Casey et al., "Reevaluation of Alcohol Synthesis and Tolerance on Brewer's Yeast", American Society of Brewing Chemists, Inc., 1985, 43(2):75-83.

(56) References Cited

OTHER PUBLICATIONS

Chen et al., "Comparison of four different chemical pretreatments of corn stover for enhancing enzymatic digestibility." Biomass and Bioenergy, 2009, 33:1381-1385.
Chen et al., "Effect of replacing helical glycine residues with alanines on reversible and irreversible stability and production of *Aspergillus awamori* glucoamylase", Protein Engineering, 1996, 9(6):499-505.
Chi et al., "High-concentration alcoholic production from hydrolysate of raw ground corn by a tetraploid yeast strain", Biotechnolgy Letters, 1993, 15(8):877-882.
Civil Docket for Case No. 4:04-cv-04202-LLP printed Jun. 23, 2006.
District Court Civil Docket No. 54: Motion to Dismiss Pursuant to FRCP 12(b)(6); Motion for a More Definite Statement Pursuant to FRCP 12(e) and Supporting Brief, by Genencor International, Inc., Entered: Feb. 14, 2005.
District Court Civil Docket No. 61: Response to Motion regarding Docket No. 53, Motion for Discovery, Requiring Plaintiff to Specify Trade Secrets Prior to Commencement of Discovery and Supporting Brief, filed by Broin and Associates, Inc., Entered: Feb. 28, 2005.
District Court Civil Docket No. 62: Reply to Motion Response regarding Docket No. 16, First Motion to Expedite Discovery and Supporting Brief, filed by Broin and Associates, Inc., Entered: Mar. 1, 2005.
District Court Civil Docket No. 67: Reply to Motion Response regarding Docket No. 53, Motion for Discovery, Requiring Plaintiff to Specify Trade Secrets Prior to Commencement of Discovery and Supporting Brief, filed by Genencor International, Inc. Entered: Mar. 2, 2005.
District Court Civil Docket No. 68: Form 35 Report of parties Planning Meeting and Scheduling Information, Entered: Mar. 3, 2005.
District Court Civil Docket No. 77: Memorandum in Opposition regarding Docket No. 54, Motion to Dismiss Pursuant to FRCP 12(b)(6); Motion for a More Definite Statement Pursuant to FRCP 12(e) and Supporting Brief, filed by Broin and Associates, inc. Entered: Mar. 9, 2005.
District Court Civil Docket No. 90: Response to Docket No. 87 Brief, Regarding Genencor's Objections to Broin's Identification of Trade Secrets, filed by Broin and Associates, inc., Entered: Apr. 11, 2005.
District Court Civil Docket No. 95: Form 35 Report of Parties Planning Meeting and Scheduling information, Entered: Apr. 18, 2005.
Dong et al., "The Neutral Detergent Fiber, Acid Detergent Fiber, Crude Fiber, and Lignin Contents of Distillers' Dried Grains with Solubles", Journal of Food Science, 1987, 52(2):403-405.
Donohoe et al., "Detecting cellulase penetration into corn stover cell walls by immuno-electron microscopy", Biotechnology and Bioengineering, 2009, 103(3):480-489.
Elander et al., "Summary of findings from the Biomass Refining Consortium for Applied Fundamentals and Innovation (CAFI): corn stover pretreatment", Cellulose, 2009, 16:649-659.
Fujio et al., "Alcohol Fermentation of Raw Cassava Starch by *Rhizopus koji* without cooking", Biotechonolgy and Bioengineering, 1984, 26:315-319.
Fujio et al., "Ethanol Fermentation of Raw Cassava Starch with *Rhizopus koji* in a Gas Circulation Type Fermentor", Biotechnology and Bioengineering, 1985, 27:1270-1273.
GCOR Lantero patent application search USPTO site.May 17, 2005.
Genencor Inventor Search, Oct. 3, 2005.
Hamdy et al., "Effects of virginiamycin on fermentation rate by yeast", Biomass and Bioenergy, 1996, 11(1):1-9.
Hamelinck et al., "Ethanol from lignocellulosic biomass: techno-economic performance in short-, middle- and long term", Biomass and Bioenergy, 2005, 28:384-410.
Han et al., "Saccharification and Ethanol Fermentation from Uncooked Starch Using *Aspergillus niger koji*", Korean J. Food Sci. Technol., 1985, 17(4):258-264.
Han et al., "Amylolysis of Raw Corn by *Aspergillus niger* for Simultaneous Ethanol Fermentation", Biotechnology and Bioengineering, 1987, 30:225-232.
Hayashida et al., "High Concentration-Ethanol Fermantation of Raw Ground Corn", Agric. Biol. Chem., 1982, 46(7):1947-1950.

Hayashida et al., "Molecular cloning of Glucoamylase 1 Gene of *Aspergillus awamori* var. kawachi for Localization of the Raw-starch-affinity Site", Agric. Biol. Chem., 1989, 53(4):923-929.
Hayashida et al., "Raw Starch-digestive Glucoamulase Productivity of Protease-less Mutant from *Asoergukkys awaniru* var. kawachi", Agric. Biol. Chem., 1981, 45(12):2675-2681.
Islam et al., "Stability of virginiamycin and penicillin during alcohol fermentation", Biomass and Bioenergy, 1999, 17: 369-376.
Iwata et al. "Purification and Characterization of Rice α-glucosidase, a key enzyme for Alcohol Fermentation of Rice Polish", Journal of Bioscience and Bioengineering, 2003, 95(1):106-108.
Jacques et al., The Alcohol Textbook, 3rd Edition, A reference for the beverage, fuel and industrial alcohol industries, Nottingham University Press 1999, Alltech Inc. 1999 (386 pages).
Jacques et al., The Alcohol Textbook, 4th Edition, A reference for the beverage, fuel and industrial alcohol industries, Nottingham University Press 2003 Alltech Inc. 2003 (446 pages).
Jensen et al., "Purification of extracellular amylolytic enzymes from the thermophilic fungus Thermomyces lanuginosus", Can. J. Microbiol., 1988, 34:218-223.
Jones, "review: Biological principles for the effects of ethanol", Enzyme Microb. Technol., 1989, 11:130-153.
Joutsjoki et al., "A Novel Glucoamylase Preparation for Grain Mash Saccharification", Biotechnology Letters, 1993, 15(3):227-282.
Kang et al., "Effect of Initiation Factor eIF-5A Depletion on Protein Synthesis and Proliferation of *Saccharomyces cerevisiae*", J. Biol. Chem., 1994, 269(6):3934-3940.
Knott et al., "Effects of the Nutrient Variability of Distiller's Solubles and Grains within Ethanol Plants and the Amount of Distiller's Solubles Blended with Distiller's Grains on Fat, Protein and Phosphorus Content of DDGS", 2004.
Knott et al., "Variation in Particle Size and Bulk Density of Distiller's Dried Grains with Solubles (DDGS) Produced by "New Generation" Ethanol Plants in Minnesota and South Dakota", 2004.
Kuyper et al., "Evolutionary engineering of mixed-sugar utilization by a xylose-fermenting *Saccharomyces cerevisiae* strain", FEMS Yeast Research, 2005, 5:925-934.
Lang et al., "Recycle Bioreactor for Bioethanol Production from Wheat Starch II. Fermentation and Economics", Energy Sources, 2001, 23:427-436.
Makarov et al., "Quality improvement of table wines following continuous clarification treatments," Kharachova Promislovist, 1976, Abstract only.
Matsumoto et al., "Industrialization of a Noncooking System for Alcoholic Fermantation from Grains", Agric. Biol. Chem., 1982, 46(6):1549-1558.
Matsuoka et al., "Alcoholic Fermentation of Sweet Potato without Cooking", J. Ferment. Technol., 1982, 60(6):599-602.
McAloon et al., "Determining the Cost of Producing Ethanol from Corn Starch and Lignocellulosic Feedstocks", Technical Report NRELTP-580-28893, 2000, www.doe.gov/bridge.
McLean et al., "Fluorometric Method for Measuring Yeast Metabolic Activity", Technical Report, 2002, 3:5-25.
McLean et al., "A Novel Method for Quantitation of Active Yeast Cells", Technical Report, 2001, 2:1-5.
Mikuni et al., "Alcohol Fermentation of Corn Starch Digested by Chalara paradoxa Amylase without Cooking", Biotechnology and Bioengineering, 1987, 29:729-732.
Minnesota Pollution Control Agency, Ethanol Production in Minnesota. Air Quality/ General #1.20/ Oct. 2002, pp. 1-4.
Morris et al., "AFM Images of Complexes between Amylose and *Aspergillus niger* Glucoamylase Mutants, Native and Mutant Starch Binding Domains: A Model for the Action of glucoamylase", Starch/Starke, 2005, 57:1-7.
Naidu et al., "Effects of Particle Size Reduction on Saccharification in Dry Grind Corn Processing", Department of Agriculture of Biological Engineering, University of Illinois at Urbana Champaign, Poster Presentation 2002 or later.
Narendranath et al., "Acetic Acid Lactic Acid Inhibition of Growth of *Saccharomyces cerevisiac* b Different Mechanisms", American Society of Brewing Chemists, Inc., 2001, 59(4):187-194.

(56) References Cited

OTHER PUBLICATIONS

Narendranath et al., "Effect of yeast inoculation rate on the metabolism of contaminating lactobailli during fermentation of corn mash", J. Ind. Microbiol. Biotechnol., 2004, 31:581-584.

Narendranath et al., "Effects of acetic acid and lactic acid on the growth of *Saccharomyces cerevisiae* in minimal medium", Journal of Industrial Microbiology & Biotechnology, 2001, 26:171-177.

Narendranath et al., "Effects of Lactobacilli on Yeast-Catalyzed Ethanol Fermentations", Applied and Environmental Microbiology, 1997, 60(11):4158-4163.

Narendranath et al., "Relationship between pH and Medium Dissolved Solids in Terms of Growth and Metabolism of Lactobacilli and *Saccharomyces cerevisiae* during Ethanol Production", Applied and Environmental Microbiology, 2005, 71(5):2239-2243.

Narendranath et al., "Urea Hydrogen Peroxide Reduces the Number of Laactobacilli, Nourishes Yeast, and Leaves No Residues in the Ethanol Fermentation", Applied and Environmental Microbiology, 2000, 66(10):4187-4192.

Narita et al., "Efficient Production of L-(+)-Lactic Acid from Raw Starch by *Streptococcus bovis* 148", Journal of Bioscience and Bioengineering, 2004, 97(6):423-425.

Neal St. Anthony, Columnists, "More profit, less waste from ethanol," Star & Tribune, Minneapolis, St. Paul, Minnesota, Date Unknown.

Porter et al., "Variability in Soy Flour Composition", JAOCS, 2003, 80(6):557-562.

Pourbafrani et al., "Production of biofuels, limonene and pectin from citrus wastes", Bioresource Technology, 2010, 101:4246-4250.

Rosentrater, "Understanding Distillers Grain Storage, Handling and Flowability Challenges", Distillers Grain Quarterly, First Quarter 2006, pp. 18-21.

Saha et al., "Raw Starch Absorption, Elution and Digestion Behavior of Glucoamylase of *Rhizopus niveus*", J. Ferment. Technol., 1983, 61(1):67-72.

Schnier et al., "Translation Initiation Factor 5A and its Hypusine Modification are Essential for Cell Viability in the yeast *Saccharomyces cerevisiae*", Molecular and Cellular Biology, 1991, 11(6):3105-3114.

Shibuya et al., "Molecular Cloning of the Glucoamylase Gene of *Aspergillus shirousami* and its Expression in *Aspergillus oryzae*", Agric. Biol. Chem., 1990, 54(8):1905-1914.

Shurson, "Overview of Swine Nutrition Research on the Value and Application of Distiller's Dried Grains with Solubles Produced by Minnesota and South Dakota Ethanol Plants", pp. 1-40 (Internet Mar. 2003).

Shurson, "The Effect of Nutrient Variability of Corn on Estimated Nutrient Variability of DDGS" University of Minnesota, Date Unknown.

Shurson, "The Value of High-Protein Distillers Coproducts in Swine Feeds", Distillers Grains Quarterly, First Quarter 2006, pp. 22.

Sigmund et al., "The Economics of Fair Play", Scientific American, 2002, pp. 83-87.

Singleton et al., Dictionary of Microbiology and Molecular Biology, 1991. John Wiley and Sons. p. 964, col. I, II. 45-48.

SpringerLink-Article, Web Page—Article—Natural Resources Research—"Ethanol Fuels: Energy Balance, Economics, and Enviornmental Impacts Are Negative", Printed Jul. 5, 2005, pp. 1-2.

Suresh et al., "Production of ethanol by raw starch hydrolysis and fermentation of damaged grains of wheat and sorghum", Bioprocess Engineering, 1999, 21:165-168.

Swanson, Company Spotlight, "Partnering in Progress", Ethanol Producer Magazine, 2004, pp. 62-64, 66-68.

Taylor et al., "Dry-Grind Process for Fuel Ethanol by Continuous Fermentation and Stripping", American Chemical Society and American Institute of Chemical Engineers, accepted for publication Mar. 27, 2000, p. A-G.

Taylor et al., "Some Properties of a Glucoamylase produced by the Thermophilic Fungus Humicola lanuginose", Carbohydrate Research, 1978, 61:301-308.

Thammarutwasik et al., "Alcoholic Fermentation of Sorghum Without Cooking", Biotechnology and Bioengineering, 1986, 28:1122-1125.

The fuel of the future, Novozymes, May 2002.

Thomas et al., "Fuel Alcohol Production: Effects of Free Amino Nitrogen on Fermentation of Very-High-Gravity Wheat Mashes", Applied and Environmental Microbiology, 1990, 56(7):2046-2050.

Tosi et al., "Purification and characterization of an extracellular glucoamylase from the thermophilic fungus Humicola grisea var. thermoidea", Can J. Microbiol., 1993, 39:846-852.

Tritto, "2 grants, 6 clients boost yields at ethanol center", St. Louis Business Journal, Nov. 26-Dec. 2, 2004.

Ueda et al., "Alchoholic Fermentation of Raw Starch without Cooking by Using Back-koji Amylase", J. Ferment. Technol., 1980, 58(3):237-242.

Ueda et al., "Direct hydrolysis of raw starch", Microbiological Sciences, 1984, 1(1):21-24.

Ueda, "Ethanol Fermentation of Starch Materials without Cooking", J. Jap. Soc. Starch Sci., 1982, 29(2):123-130, (English Abstract).

Van Maris et al., "Alcoholic fermentation of carbon sources in biomass hydrolysates by *Saccharomyces cerevisiae*: current status", Antonie van Leeuwenhoek, 2006, 90:391-418.

Van Uden et al., "Effects of ethanol on yeast performance; targets and underlying mechanisms". European Brewery Convention, Proceedings of the $19^{th}$ Congress, London 1983, pp. 137-144.

Wang. "Argonne National Laboratory Ethanol Study: Key points." Office of Energy Efficiency and Renewal Energy—U.S. Department of Energy, pp. 1-3, 2005.

Weiss et al. "Distillers Grains", eXtension, Last Updated May 12, 2009, pp. 1-6, Printed May 8, 2010.

Weller et al., "Fuel Ethanol from Raw Corn by Aspergilli Hydrolysis with Concurrent Yeast Fermentation", Biotechnology and Bioengineering Symp., 1983, 13:437-447.

www.nrel.gov/docs/fy02osti/31195.pdf. Biofuels News. vol. 4. No. 3. Fall 2001.

Yue et al., "Functionality of resistant starch in food applications", National Starch & Chemical (reprinted from Dec. 1998 issue of Food Australia) (1999).

Zheng et al., "Enzymatic saccharification of dilute acid pretreated saline crops for fermentable sugar production", Applied Energy, 2009, 86:2459-2465.

Ziffer et al., "Temperature Effects in Ethanol Fermentation High Corn Media", Biotechnology Letters, 1982, 4(12):809-814.

De Mancilha, et al, "Evaluation of Ion Exchange Resins for Removal of Inhibitory Compounds from Corn Stover Hydrolyzate for Xylitol Fermentation," Biotechnology Progress, (2003), 19:1837-1841.

Gulati, et al., "Assessment of Ethanol Production Options for Corn Products," Bioresource Technology, (1996), 58:253-264.

Jeffries, T.W., et al., Fermentation of Hemicellulosic Sugars and Sugar Mixtures by Candida shehatae, Biotechnology and Bioengineering, 31:502-506 (1988).

Maier, et al., "Low-Temperature Drying of the 1992 Indiana Corn Crop," Grain Quality Fact Sheet #5. Purdue University Cooperative Extension Service, West Lafayette, Indiana, (1992), pp. 1-8, http://www.extension.purdue.edu/extmedia/GQ/GQ-5.HTML.

Nigam, et al., "Enzyme and microbial systems involved in starch processing," Enzyme and Microbial Technology, (1995), 17:770-778.

U.S. Appl. No. 12/827,948, filed Jun. 2010, Bootsma et al.
U.S. Appl. No. 12/828,028, filed Jun. 2010, Bootsma et al.
U.S. Appl. No. 13/209,170, filed Aug. 2011, Bly et al.
U.S. Appl. No. 13/798,617, filed Mar. 2013, Narendranath.
U.S. Appl. No. 13/804,364, filed Mar. 2013, Narendranath et al.
U.S. Appl. No. 13/980,255, filed Jul. 2013, Narendranath et al.
U.S. appl. No. 14/130,878, filed Jan. 2014, McDonald et al.

Adney, B. et al., "Measurement of Cellulase Activities", Technical Report NREL/TP-510-42628 (2008) Cover; p. 1-8.

Caparros, S. et al., "Xylooligosaccharides Production from Arundo donax", J. Agric. Food Chem. 55 (2007): p. 5536-5543.

Cort, J. et al., "Minimize Scale-Up Risk", www.aiche.org/cep, (2010): p. 39-49.

Demain, A.L. et al., "Cellulose, Clostridia, and Ethanol", Microbiology and Molecular Biology Reviews 69(1) (2005): p. 124-154.

(56) References Cited

OTHER PUBLICATIONS

Dien, B.S. et al., "Enzyme characterization for hydrolysis of AFEX and liquid hot-water pretreated distillers' grains and their conversion to ethanol", Bioresource Technology 99 (2008): p. 5216-5225.
Gibbons, W.R. et al., "Fuel Ethanol and High Protein Feed from Corn and Corn-Whey Mixtures in a Farm-Scale Plant", Biotechnology and Bioengineering XXV (1983): p. 2127-2148.
Goodman, B. J., "FY 1988 Ethanol from Biomass Annual Report" (1989): p. 1-458.
Grohmann, K. et al., "Optimization of Dilute Acid Pretreatment of Biomass", Biotechnology and Bioengineering Symp. 15 (1985): p. 59-80.
Grohmann, K. et al., "Dilute Acid Pretreatment of Biomass at High Solids Concentrations", Biotechnology and Bioengineering Symp. 17 (1986): p. 135-151.
Humbird, D. et al., "Process Design and Economics for Biochemical Conversion of Lignocellulosic Biomass to Ethanol: Dilute-Acid Pretreatment and Enzymatic Hydrolysis of Corn Stover", National Renewable Energy Laboratory (2011): Covers with Introduction; p. 1-114.
Jeoh, T. "Steam Explosion Pretreatment of Cotton Gin Waste for Fuel Ethanol Production", Thesis submitted to Virginia Polytechnic Institute and State University (1998): Cover with Introduction; p. 1-138.
Jorgensen, H. et al., "Enzymatic conversion of lignocellulose into fermentable sugars: challenges and opportunities", Biofuels, Bioprod. Bioref 1 (2001): p. 119-134.
Kumar, R. et al., "Effect of Enzyme Supplementation at Moderate Cellulase Loadings on Initial Glucose and Xylose Release from Corn Stover Solids Pretreated by Leading Technologies", Biotechnology and Bioengineering 102(2) (2009); p. 457-467.
Larsen, J. et al., "The IBUS Process—Lignocellulosic Bioethanol Close to a Commercial Reality", Chem. Eng. Technol. 31(5) (2008): p. 765-772.
Lynd, L.R. et al. "Consolidated bioprocessing of cellulosic biomass: an update", Current Opinion in Biotechnology 16 (2005): p. 577-583.
Mosier, N. et at, "Features of promising technologies for pretreatment of lignocellulosic biomass", Bioresource Technology 96 (2005): p. 673-686.
McMillan, J.D. "Processes for Pretreating Lignocellulosic Biomass: A Review", National Renewable Energy Laboratory (1992): Covers with Introduction; p. 1-44.
Nandini, C. et al. "Carbohydrate composition of wheat, wheat bran, sorghum and bajra with good chapatti/roti (Indian flat bread) making quality", Food Chemistry 73 (2001): p. 197-203.
Sanchez, O.J. et al., "Trends in biotechnological production of fuel ethanol from different feedstocks", Bioresource Technology 99 (2008): p. 5270-5295.
Saska, M. et al., "Aqueous Extraction of Sugarcane Bagasse Hemicellulose and Production of Xylose Syrup", Biotechnology and Bioengineering 45 (1995): p. 517-523.
Sepulveda-Huerta, E. et al. "Production of detoxified sorghum straw hydrolysates for fermentative purposes", Journal of the Science of Food and Agriculture 86 (2006): p. 2579-2586.
Spindler, D. et al., "Evaluation of Pretreated Woody Crops for the Simultaneous Saccharification and Fermentation Process", Ethanol from Biomass. FY 1988, Annual Report (1989): p. B33-B43.
Taherzadeh, M.J. et al., "Acid-based Hydrolysis Processes for Ethanol from Lignocellulosic Materials: A Review", BioResources 2(3) (2007): p. 472-499.
Taherzadeh, M.J. et al., "Enzyme-based Hydrolysis Processes for Ethanol from Lignocellulosic Materials: A Review", BioResources 2(4) (2007): p. 707-738.
Texeira, R.H. et al., "Ethanol Annual Report FY 1990", (1991): p. 1-346.
Torget, R. et al., "Dilute Acid Pretreatment of Short Rotation Woody and Herbaceous Crops", Applied Biochemistry and Biotechnology 24/25 (1990): p. 115-126.
Torget, R. et al., "Initial Design of a Dilute Sulfuric Acid Pretreatment Process for Aspen Wood Chips", Solar Energy Research Institute (1988): p. 89-104.
Torget, R. et al., "Dilute Acid Pretreatment of Corn Cobs, Corn Stover, and Short-Rotation Crops", FY 1990 Ethanol Annual Report (1991): p. 71-81.
Weil, J. et al., "Pretreatment of Corn Fiber by Pressure Cooking in Water", Applied Biochemistry and Biotechnology 73 (1998): p. 1-17.
Wyman, Charles E., "What is (and is not) vital to advancing cellulosic ethanol", Trends in Biotechnology 25(4) (2007): p. 153-157.
Wyman, C.E. et al., "Coordinated development of leading biomass pretreatment technologies", Bioresource Technology 96 (2005): p. 1959-1966.
Yang, B. et al., "Pretreatment: the key to unlocking low-cost cellulosic ethanol", Biofuels, Bioprod. Bioref. 2 (2008): p. 26-40.
Zhang, Y-H.P. et al., "Outlook for cellulose improvement: Screening and selection strategies", Biotechnology Advances 24 (2006): p. 452-481.
Zhang, Y.P. et al., "Toward an Aggregated Understanding of Enzymatic Hydrolysis of Cellulose: Noncomplexed Cellulase Systems", Biotechnology and Bioengineering 88(7) (2004): p. 797-824.
Bellissimi, Eleonora et al., *Effects of acetic acid on the kinetics of xylose fermentation by an engineered, xylose-isomerase-based Saccharomyces cerevisiae strain*, FEMS Yeast Res 9 (2009): 358-364.

\* cited by examiner

OPERATING CONDITION

Temperature (°C)

OPERATING CONDITION pH

OPERATING CONDITION

Yeast Loading (g/L)

OPERATING CONDITION

Time (h)

SYSTEM FOR FERMENTATION OF BIOMASS FOR THE PRODUCTION OF ETHANOL

CROSS-REFERENCE TO RELATED APPLICATIONS

The present application claims priority to and incorporates by reference each of the following applications: (a) U.S. Provisional Application Ser. No. 61/157,140, titled Process for Fermenting Pentose in Biomass, filed on Mar. 3, 2009; (b) U.S. Provisional Application Ser. No. 61/157,142, titled Continuous Fermentation of a Liquid Hydrolysate Containing Pentose, filed on Mar. 3, 2009; and (c) U.S. Provisional Application Ser. No. 61/157,137, titled Concentration of Pentose Liquor, filed on Mar. 3, 2009.

The present application relates to and incorporates by reference the following applications: (a) U.S. application Ser. No. 12/716,984, titled System for Pre-Treatment of Biomass for the Production of Ethanol, filed on Mar. 3, 2010; (b) U.S. application Ser. No. 12/716,989, titled System for Treatment of Biomass to Facilitate the Production of Ethanol, filed on Mar. 3, 2010; and (c) U.S. application Ser. No. 12/717,002, titled System for Management of Yeast to Facilitate the Production of Ethanol, filed on Mar. 3, 2010.

FIELD

The present invention relates to a system for fermentation of biomass in the production of ethanol. The present invention also relates to a system for fermentation of biomass that has been pre-treated and separated into a first component and a second component. The present invention further relates to a system for fermentation of a first component of biomass using an ethanologen capable of fermenting xylose into ethanol.

BACKGROUND

Ethanol can be produced from grain-based feedstocks (e.g. corn, sorghum/milo, barley, wheat, soybeans, etc.), from sugar (e.g. from sugar cane, sugar beets, etc.), and from biomass (e.g. from lignocellulosic feedstocks such as switchgrass, corn cobs and stover, wood or other plant material).

Biomass comprises plant matter that can be suitable for direct use as a fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during or after harvesting of the corn kernels, fiber from the corn kernel, switchgrass, farm or agricultural residue, wood chips or other wood waste, and other plant matter (grown for processing into bioproducts or for other purposes). In order to be used or processed, biomass will be harvested and collected from the field and transported to the location where it is to be used or processed.

In a conventional ethanol plant producing ethanol from corn, ethanol is produced from starch. Corn kernels are cleaned and milled to prepare starch-containing material for processing. (Corn kernels can also be fractionated to separate the starch-containing material (e.g. endosperm) from other matter (such as fiber and germ).) The starch-containing material is slurried with water and liquefied to facilitate saccharification where the starch is converted into sugar (e.g. glucose) and fermentation where the sugar is converted by an ethanologen (e.g. yeast) into ethanol. The product of fermentation (i.e. fermentation product) is beer, which comprises a liquid component containing ethanol and water and soluble components, and a solids component containing unfermented particulate matter (among other things). The fermentation product is sent to a distillation system. In the distillation system, the fermentation product is distilled and dehydrated into ethanol. The residual matter (e.g. whole stillage) comprises water, soluble components, oil and unfermented solids (i.e. the solids component of the beer with substantially all ethanol removed that can be dried into dried distillers grains (DDG) and sold as an animal feed product). Other co-products, for example syrup (and oil contained in the syrup), can also be recovered from the stillage. Water removed from the fermentation product in distillation can be treated for re-use at the plant.

In a biorefinery configured to produce ethanol from biomass, ethanol is produced from lignocellulosic material. Lignocellulosic biomass typically comprises cellulose, hemicellulose and lignin. Cellulose (a type of glucan) is a polysaccharide comprising hexose (C6) sugar monomers such as glucose linked in linear chains. Hemicellulose is a branched chain polysaccharide that may comprise several different pentose (C5) sugar monomers (such as xylose and arabinose) and small amounts of hexose (C6) sugar monomers in branched chains.

The biomass is prepared so that sugars in the lignocellulosic material (such as glucose from the cellulose and xylose from the hemicellulose) can be made accessible and fermented into a fermentation product from which ethanol can be recovered. After fermentation the fermentation product is sent to the distillation system, where the ethanol is recovered by distillation and dehydration. Other bioproducts such as lignin and organic acids may also be recovered as by-products or co-products during the processing of biomass into ethanol. Determination of how to more efficiently prepare and treat the biomass for production into ethanol will depend upon the source and type or composition of the biomass. Biomass of different types or from different sources is likely to vary in properties and composition (e.g. relative amounts of cellulose, hemicellulose, lignin and other components). For example the composition of wood chips will differ from the composition of corn cobs or switchgrass.

It would be advantageous to provide for a system for treatment of biomass to facilitate the production of ethanol. It would also be advantageous to provide for a system to fermenting biomass for the production of ethanol. It would further be advantageous to provide for a system that provided one or more of features to facilitate improvement in the efficiency and yield of cellulosic ethanol from biomass.

SUMMARY

The present invention relates to a method for producing a fermentation product in a fermentation system from biomass that has been pre-treated and separated into a first component and a second component. The method comprises the steps of supplying the first component to the fermentation system; providing an ethanologen to the fermentation system; maintaining the first component and ethanologen in the fermentation system at a temperature of between about 26 and about 37 degrees Celsius and at a pH of between about 4.5 and about 6.0 for a time of no less than 18 hours; and recovering the fermentation product from the fermentation system. The ethanologen is supplied to the fermentation system in a concentration of less than 150 grams of ethanologen on a dry basis per liter of first component. The biomass comprises lignocellulosic material; the lignocellulosic material comprises at least one of corn cobs, corn plant husks, corn plant leaves and corn plant stalks. The first component comprises pentose; the pentose comprises xylose. The ethanologen is capable of fermenting xylose into ethanol.

The present invention also relates to a fermentation system configured to produce a fermentation product from biomass that has been pre-treated and separated into a first component and a second component. The system comprises a first vessel configured to receive the first component and an ethanologen and a second vessel configured to propagate the ethanologen for supply to the first vessel. The first vessel is configured to maintain the first component and ethanologen at a temperature of between about 31 and about 34 degrees Celsius and at a pH of between about 5.2 and about 5.8 for a time of no less than 18 hours. The biomass comprises lignocellulosic material; the lignocellulosic material comprises at least one of corn cobs, corn plant husks, corn plant leaves and corn plant stalks. The first component comprises pentose; the pentose comprises xylose.

The present invention further relates to a biorefinery for producing a fermentation product from biomass. The biorefinery comprises a preparation system to prepare the biomass into prepared biomass; a pre-treatment system to pre-treat the prepared biomass with a dilute acid for separation into a first component from which pentose can accessed for fermentation and a second component from which hexose can be made available for fermentation; a first treatment system to treat the first component into a treated first component by removing removed components from the first component; a first fermentation system to produce a first fermentation product from the pentose by supplying an ethanologen and maintaining the first component and ethanologen at a temperature of between about 26 and about 37 degrees Celsius and at a pH of between about 4.5 and about 6.0 for a time of no less than 18 hours; a distillation system to recover ethanol from the first fermentation product; and a treatment system to process removed components. The biomass comprises lignocellulosic material; the lignocellulosic material comprises at least one of corn cobs, corn plant husks, corn plant leaves and corn plant stalks.

BRIEF DESCRIPTION OF THE FIGURES AND TABLES

TABLES 1A and 1B list the composition of biomass comprising lignocellulosic plant material from the corn plant according to exemplary and representative embodiments.

TABLES 2A and 2B list the composition of the liquid component of pre-treated biomass according to exemplary and representative embodiments.

TABLES 3A and 3B list the composition of the solids component of pre-treated biomass according to exemplary and representative embodiments.

TABLES 4 through 7 provide data and results relating to the use of the fermentation system according to an exemplary embodiment.

DETAILED DESCRIPTION

Figure 1A:
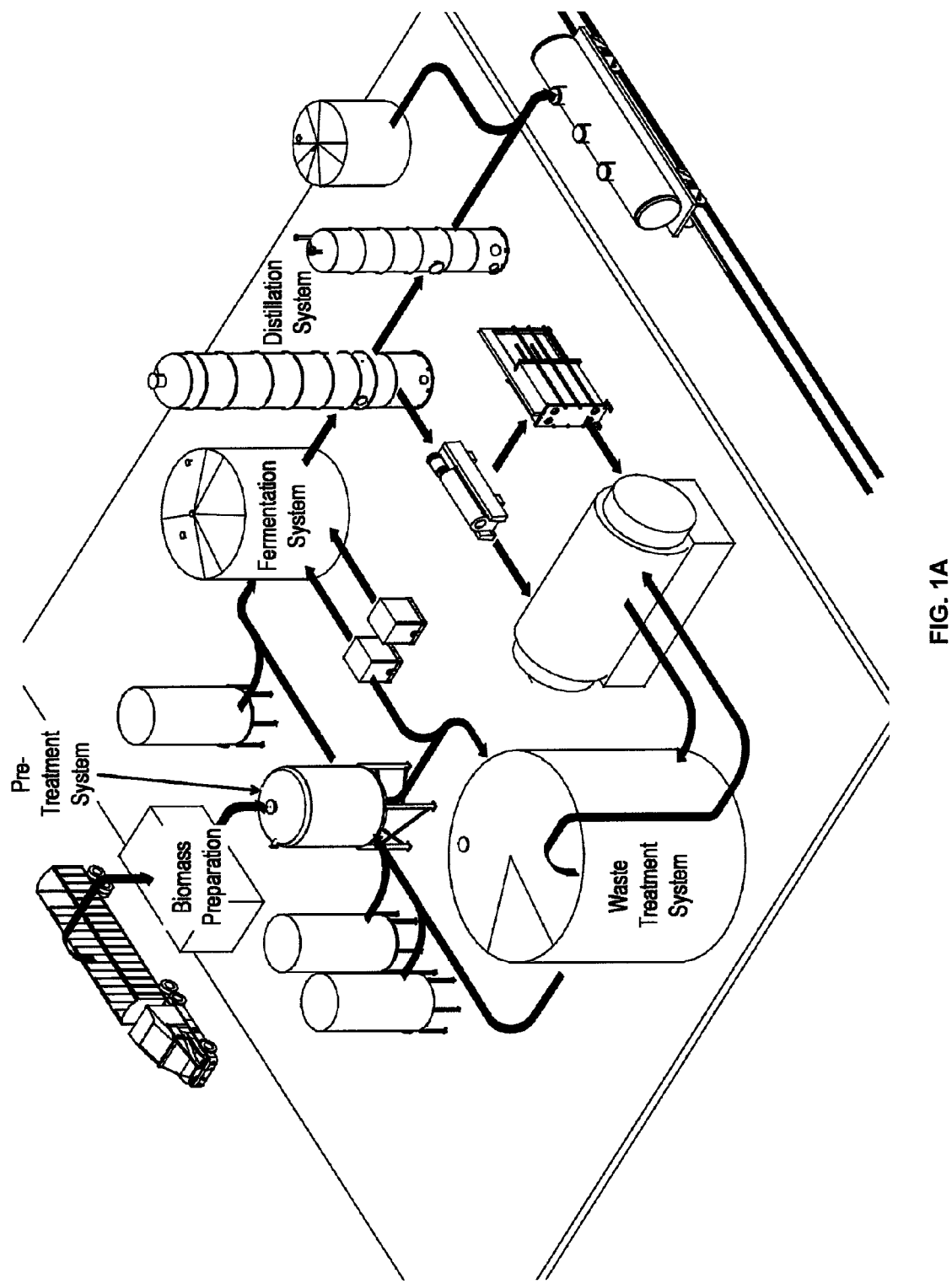
FIG. 1A is a perspective view of a biorefinery comprising a cellulosic ethanol production facility.

Referring to FIG. 1A, a biorefinery configured to produce ethanol from biomass is shown.

According to an exemplary embodiment, the biorefinery is configured to produce ethanol from biomass in the form of a lignocellulosic feedstock such as plant material from the corn plant (e.g. corn cobs and corn stover). Lignocellulosic feedstock such as lignocellulosic material from the corn plant comprises cellulose (from which C6 sugars such as glucose can be made available) and/or hemicellulose (from which C5 sugars such as xylose and arabinose can be made available).

As shown in FIG. 1A, the biorefinery comprises an area where biomass is delivered and prepared to be supplied to the cellulosic ethanol production facility. The cellulosic ethanol production facility comprises apparatus for preparation, pre-treatment and treatment of the biomass into treated biomass suitable for fermentation into fermentation product in a fermentation system. The facility comprises a distillation system in which the fermentation product is distilled and dehydrated into ethanol. As shown in FIG. 1A, the biorefinery may also comprise a waste treatment system (shown as comprising an anaerobic digester and a generator). According to other alternative embodiments, the waste treatment system may comprise other equipment configured to treat, process and recover components from the cellulosic ethanol production process, such as a solid/waste fuel boiler, anaerobic digester, aerobic digester or other biochemical or chemical reactors.

Figure 1B:
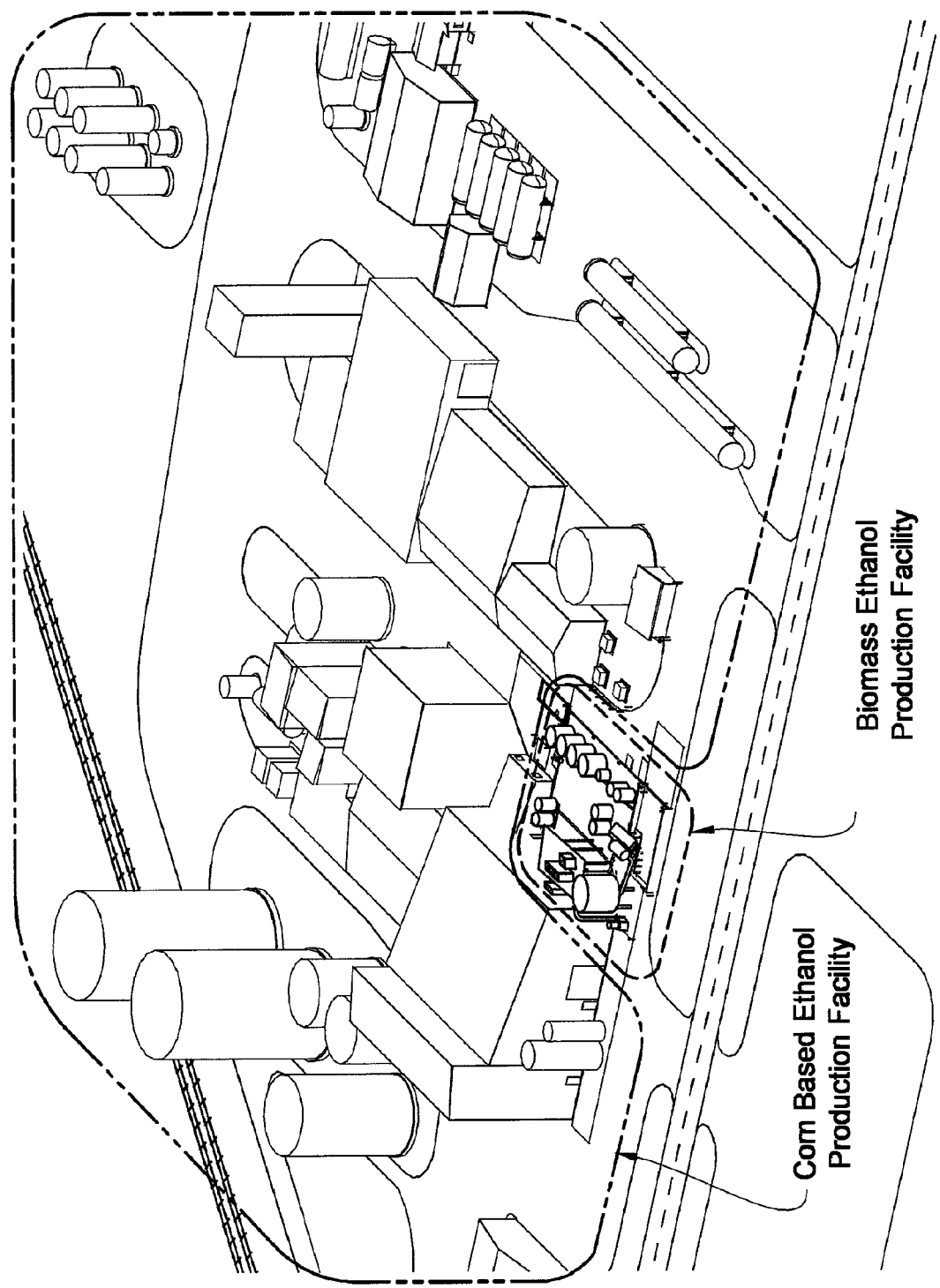
FIG. 1B is a perspective view of a biorefinery comprising a cellulosic ethanol production facility and a corn-based ethanol production facility.

As shown in FIG. 1B, according to an exemplary embodiment, a biorefinery may comprise a cellulosic ethanol production facility (which produces ethanol from lignocellulosic material and components of the corn plant) co-located with a corn-based ethanol production facility (which produces ethanol from starch contained in the endosperm component of the corn kernel). As indicated in FIG. 1B, by co-locating the two ethanol production facilities, certain plant systems may be shared, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared for milling (e.g. by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g. a cellulosic ethanol production facility) may be co-located with other types of plants and facilities, for example an electric power plant, a waste treatment facility, a lumber mill, a paper plant or a facility that processes agricultural products.

Figure 2:
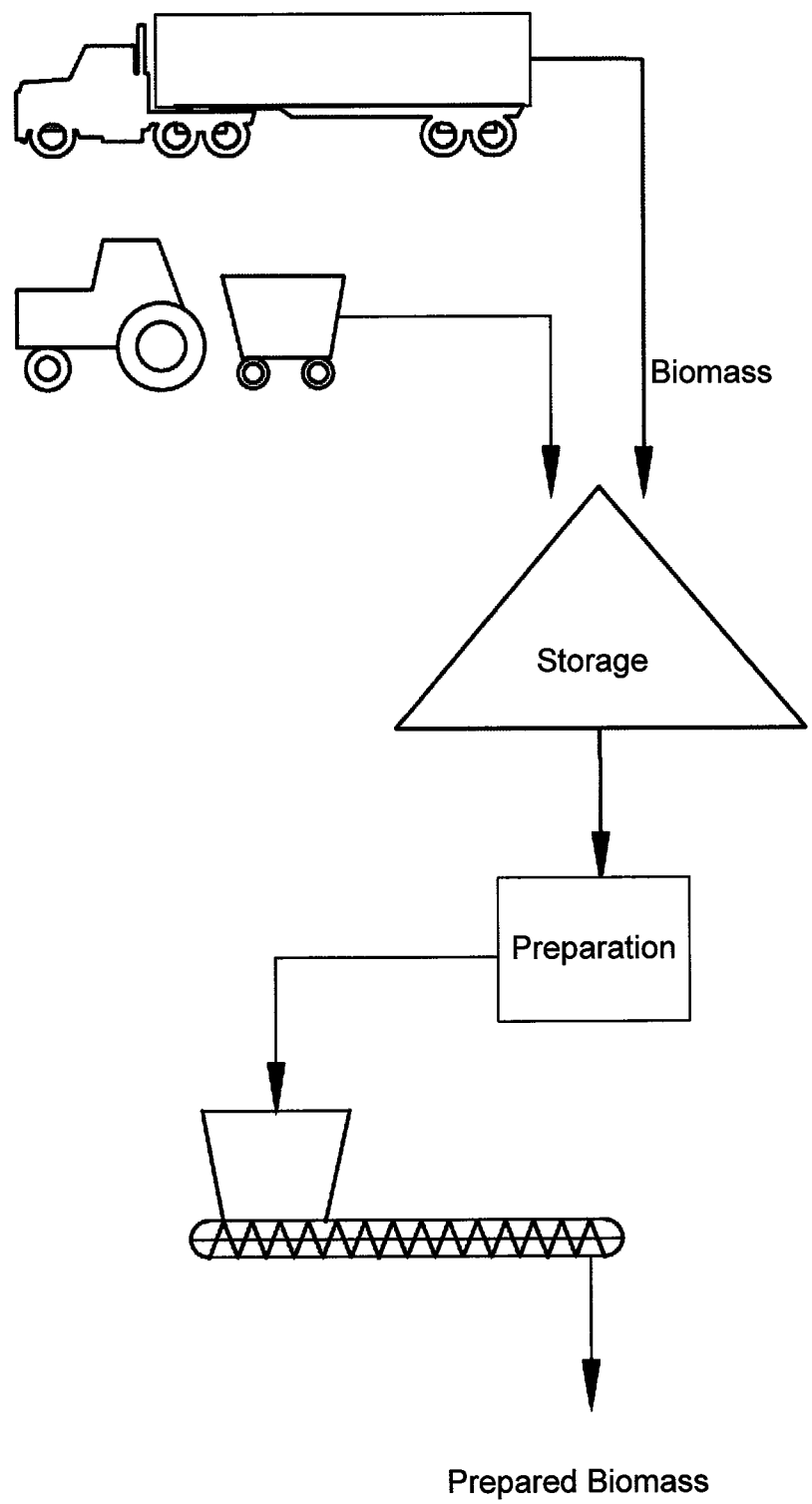
FIG. 2 is a schematic diagram of a system for receipt and preparation of biomass for a cellulosic ethanol production facility.

Referring to FIG. 2, a system for preparation of biomass delivered to the biorefinery is shown. The biomass preparation system may comprise apparatus for receipt/unloading of the biomass, cleaning (i.e. removal of foreign matter), grinding (i.e. milling, reduction or densification), and transport and conveyance for processing at the plant. According to an exemplary embodiment, biomass in the form of corn cobs and stover may be delivered to the biorefinery and stored (e.g. in bales, piles or bins, etc.) and managed for use at the facility. According to a preferred embodiment, the biomass may comprise at least 20 to 30 percent corn cobs (by weight) with corn stover and other matter. According to other exemplary embodiments, the preparation system of the biorefinery may be configured to prepare any of a wide variety of types of biomass (i.e. plant material) for treatment and processing into ethanol and other bioproducts at the plant.

Figure 3:
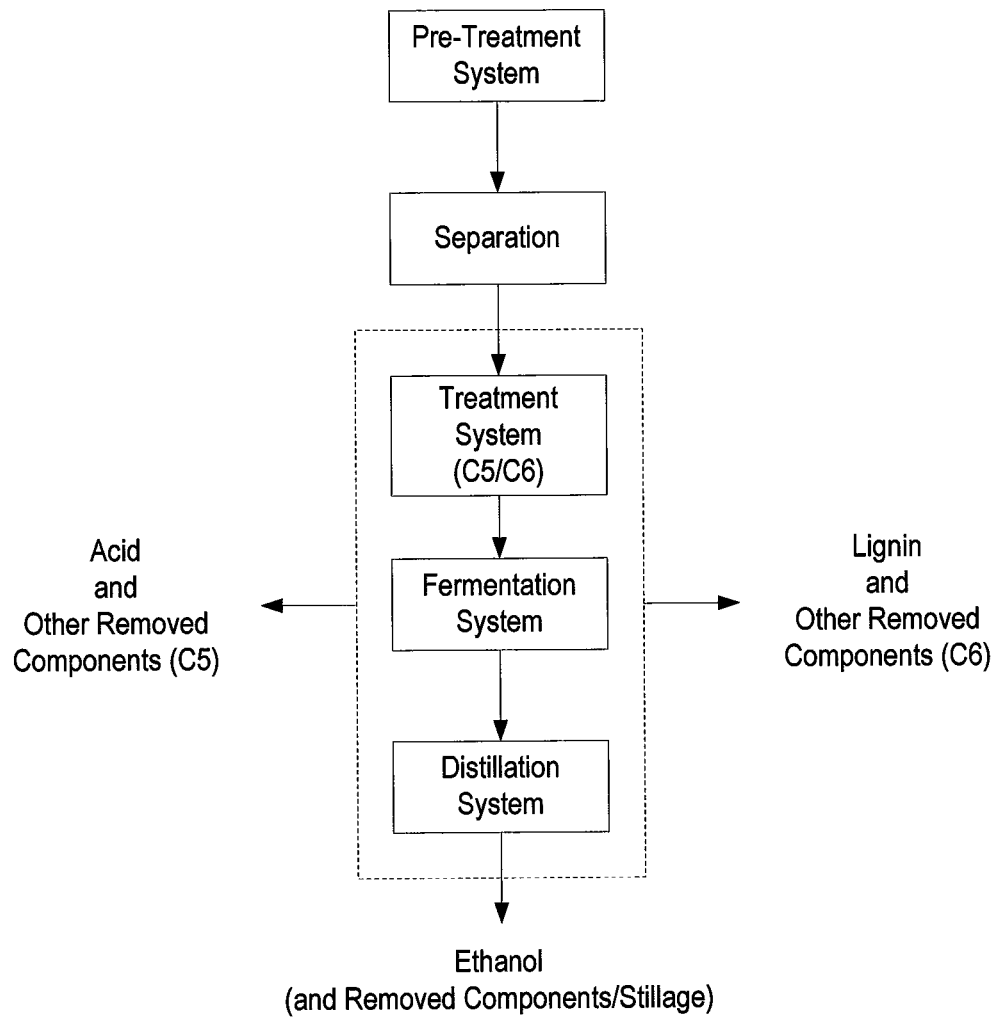
FIG. 3 is a schematic block diagram of a system for the production of ethanol from biomass.

Referring to FIG. 3, a schematic diagram of the cellulosic ethanol production facility is shown. According to a preferred embodiment, biomass comprising plant material from the corn plant is prepared and cleaned at a preparation system. After preparation, the biomass is mixed with water into a slurry and is pre-treated at a pre-treatment system. In the pre-treatment system, the biomass is broken down (e.g. by hydrolysis) to facilitate separation into a liquid component (e.g. a stream comprising the C5 sugars) and a solids component (e.g. a stream comprising cellulose from which the C6 sugars can be made available). In one embodiment, the pre-treatment comprises pre-treating the biomass with an aqueous composition comprising an acid having a concentration of about 0.05 to about 2.0 percent by weight at a temperature of about 130° to about 170° C. for a period of time sufficient to produce a solids component and an aqueous component, which aqueous component contains xylose. According to exemplary embodiments, an acid such as sulfuric acid, hydrochloric acid, nitric acid, phosphoric acid, acetic acid, etc. (or a formulation/mixture of acids) can be applied to the biomass. Pre-treatment under these conditions results in maximal xylose yield with a suitably low level of inhibitor production. Inhibitors may include, for example, furfural, hydroxymethylfurfural, or organic acids. The C5-sugar-containing liquid component (C5 stream) and C6-sugar-containing solids component (C6 stream) can be treated (as may be suitable) and fermented in a fermentation system. Fermentation product from the fermentation system is supplied to a distillation system where the ethanol is recovered.

Figures 4A, 4B, 4C:
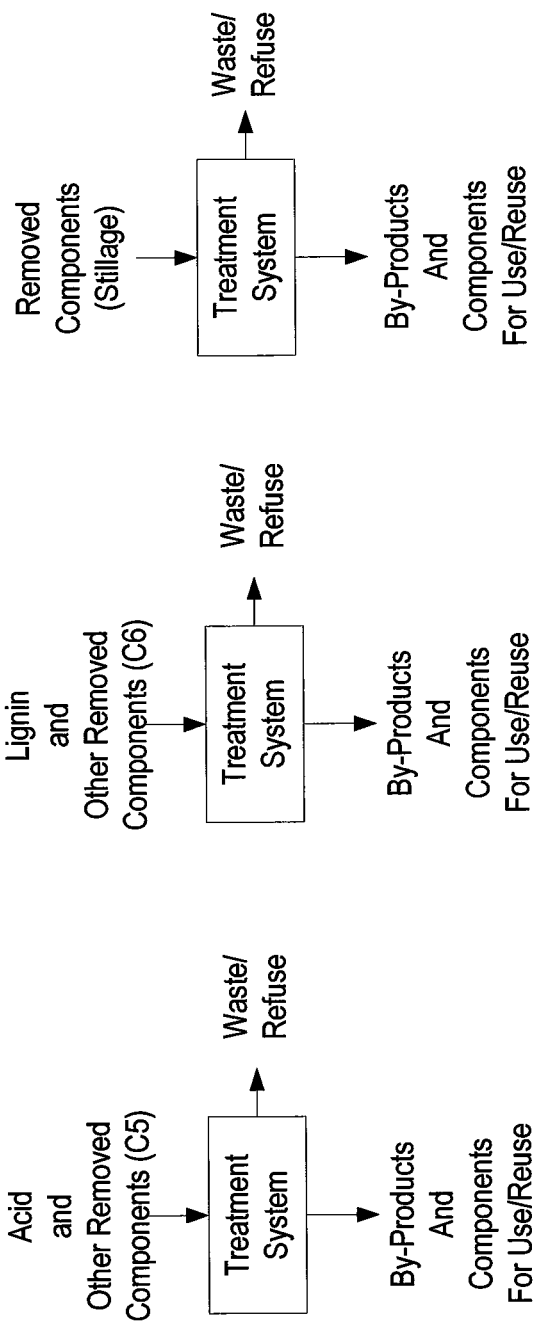
FIGS. 4A, 4B and 4C are schematic block diagrams of systems for treatment and processing of components from the production of ethanol from biomass.

As shown in FIGS. 3 and 4A, removed components from treatment of the C5 stream can be treated or processed to recover by-products, such as organic acids and furfural. As shown in FIGS. 3 and 4B, removed components from treatment of the C6 stream, such as lignin or other components, can be treated or processed into bioproducts or into fuel (such as lignin for a solid fuel boiler or methane produced by treatment of residual/removed matter such as acids and lignin in an anaerobic digester). As shown in FIGS. 4A, 4B and 4C, components removed during treatment and production of ethanol from the biomass from either or both the C5 stream and the C6 stream (or at distillation) may be processed into bioproducts (e.g. by-products or co-products) or recovered for use or reuse. As shown in FIG. 4C, removed components from the distillation system (such as stillage or removed solids) or from the treatment of the fermentation product before distillation (e.g. removed solids and particulate matter, which may comprise residual lignin, etc.) can be treated or processed into bioproducts or fuel (e.g. methane produced in an anaerobic digester).

According to a preferred embodiment, the biomass comprises plant material from the corn plant, such as corn cobs, husks and leaves and stalks (e.g. at least upper half or three-quarters portion of the stalk); the composition of the plant material (i.e. cellulose, hemicellulose and lignin) will be approximately as indicated in TABLES 1A and 1B (i.e. after at least initial preparation of the biomass, including removal of any foreign matter). According to a preferred embodiment, the plant material comprises corn cobs, husks/leaves and stalks; for example, the plant material may comprise (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any other combinations of cobs, husks/leaves and stalks from the corn plant. See TABLE 1A. According to an alternative embodiment, the lignocellulosic plant material may comprise fiber from the corn kernel (e.g. in some combination with other plant material). TABLE 1B provides typical and expected ranges believed to be representative of the composition of biomass comprising lignocellulosic material from the corn plant. According to exemplary embodiments, the lignocellulosic plant material of the biomass (from the corn plant) will comprise (by weight) cellulose at about 30 to 55 percent, hemicellulose at about 20 to 50 percent, and lignin at about 10 to 25 percent; according to a particularly preferred embodiment, the lignocellulosic plant material of the biomass (i.e. cobs, husks/leaves and stalk portions from the corn plant) will comprise (by weight) cellulose at about 35 to 45 percent, hemicellulose at about 24 to 42 percent, and lignin at about 12 to 20 percent. According to a particularly preferred embodiment, pre-treatment of the biomass will yield a liquid component that comprises (by weight) xylose at no less than 1.0 percent and a solids component that comprises (by weight) cellulose (from which glucose can be made available) at no less than 45 percent.

Figure 5A:
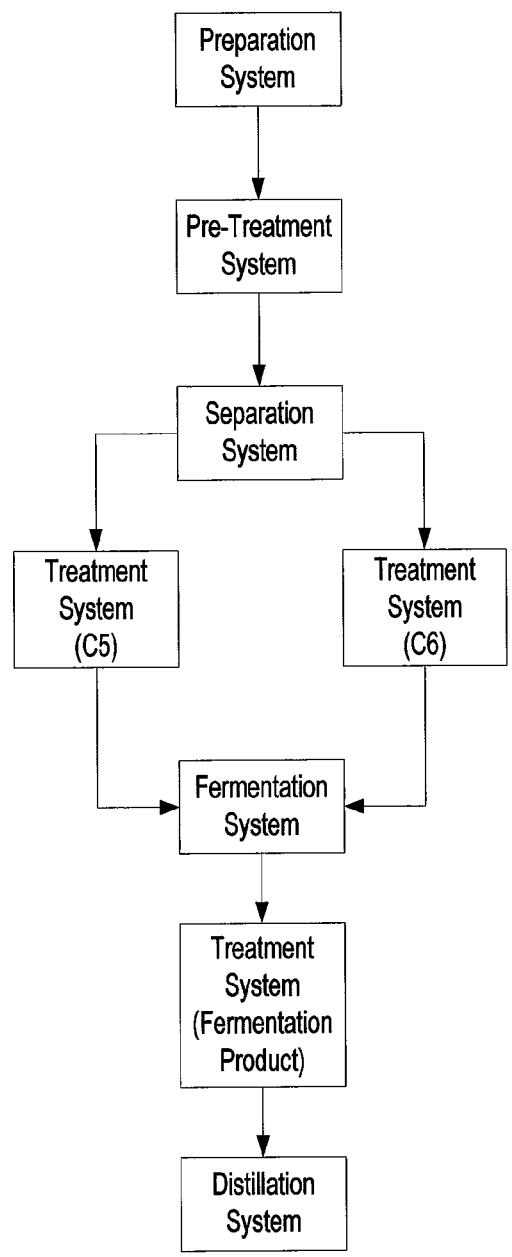
FIGS. 5A and 5B are schematic diagrams of the process flow for systems for the production of ethanol from biomass.
Figure 5B:
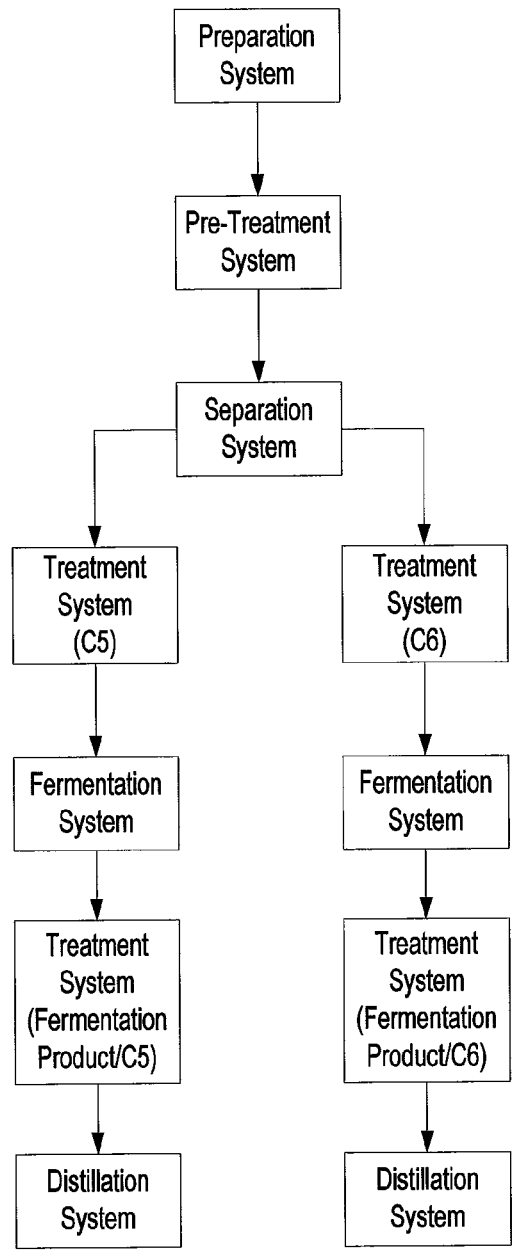

Referring to FIGS. 5A and 5B, exemplary embodiments of systems for the production of ethanol from biomass are shown. As shown in FIGS. 5A and 5B, biomass is pre-treated in a pre-treatment system and then separated into a liquid component and a solids component.

According to a preferred embodiment, in the pre-treatment system an acid will be applied to the prepared biomass to facilitate the break down of the biomass for separation into the liquid component (C5 stream from which fermentable C5 sugars can be recovered) and the solids component (C6 stream from which fermentable C6 sugars can be accessed). According to a preferred embodiment, the acid can be applied to the biomass in a reaction vessel under determined operating conditions (i.e. acid concentration, pH, temperature, time, pressure, solids loading, flow rate, supply of process water or steam, etc.) and the biomass can be agitated/mixed in the reaction vessel to facilitate the break down of the biomass.

According to exemplary embodiments, an acid such as sulfuric acid, hydrochloric acid, nitric acid, phosphoric acid, acetic acid, etc. (or a formulation/mixture of acids) can be applied to the biomass. According to a particularly preferred embodiment, sulfuric acid will be applied to the biomass in pre-treatment.

The liquid component (C5 stream) comprises water, dissolved sugars (such as xylose, arabinose and glucose) to be made available for fermentation into ethanol, acids and other soluble components recovered from the hemicellulose. (TABLE 2B provides typical and expected ranges believed to be representative of the composition of biomass comprising lignocellulosic material from the corn plant.) According to an exemplary embodiment, the liquid component may comprise approximately 5 to 7 percent solids (i.e. suspended/residual solids such as partially-hydrolyzed hemicellulose, cellulose and lignin). According to a particularly preferred embodiment, the liquid component will comprise at least 2 to 4 percent xylose (by weight); according to other exemplary embodiments, the liquid component will comprise no less than 1 to 2 percent xylose (by weight). TABLES 2A and 2B list the composition of the liquid component of pre-treated biomass (from prepared biomass as indicated in TABLES 1A and 1B) according to exemplary and representative embodiments.

The solids component (C6 stream) comprises water, acids and solids such as cellulose from which sugar, such as glucose, can be made available for fermentation into ethanol, and lignin. (TABLE 3B provides typical and expected ranges believed to be representative of the composition of biomass comprising lignocellulosic material from the corn plant.) According to an exemplary embodiment, the solids component may comprise approximately 10 to 40 percent solids (by weight) (after separation); according to a particularly preferred embodiment, the solids component will comprise approximately 20 to 30 percent solids (by weight). According to a preferred embodiment, the solids in the solids component comprise no less than 30 percent cellulose and the solids component may also comprise other dissolved sugars (e.g. glucose and xylose). TABLES 3A and 3B list the composition of the solids component of pre-treated biomass (from prepared biomass as indicated in TABLES 1A and 1B) according to exemplary and representative embodiments.

During pre-treatment, the severity of operating conditions (such as pH, temperature and time) may cause formation of components that are inhibitory to fermentation. For example, under some conditions, the dehydration of C5 sugars (such as xylose or arabinose) may cause the formation of furfural and/or hydroxymethylfurfural (HMF). Acetic acid may also be formed, for example when acetate is released during the break down of cellulose in pre-treatment. Sulfuric acid, which may be added to prepared biomass to facilitate pre-treatment, if not removed or neutralized, may also be inhibitory to fermentation. According to an exemplary embodiment, by adjusting pre-treatment conditions (such as pH, temperature and time), the formation of inhibitors can be reduced or managed; according to other exemplary embodiments, components of the pre-treated biomass may be given further treatment to remove or reduce the level of inhibitors (or other undesirable matter).

Referring to FIGS. 5A and 5B, after pre-treatment and separation the C5 stream and the C6 stream are processed separately; as shown, the C5 stream and the C6 stream may be processed separately prior to co-fermentation (C5/C6 fermentation as shown in FIG. 5A) or processed separately including separate fermentation (separate C5 fermentation and C6 fermentation as shown in FIG. 5B).

Treatment of the C5 stream (liquid component) of the biomass may be performed in an effort to remove components that are inhibitory to efficient fermentation (e.g. furfural, HMF, sulfuric acid and acetic acid) and residual lignin (or other matter) that may not be fermentable from the C5 sugar component so that the sugars (e.g. xylose, arabinose, as well as other sugars such as glucose) are available for fermentation. The C5 sugars in the C5 stream may also be concentrated to improve the efficiency of fermentation (e.g. to improve the titer of ethanol for distillation).

Treatment of the C6 stream (solids component) of the biomass may be performed to make the C6 sugars available for fermentation. According to a preferred embodiment, hydrolysis (such as enzyme hydrolysis) may be performed to access the C6 sugars in the cellulose; treatment may also be performed in an effort to remove lignin and other non-fermentable components in the C6 stream (or to remove components such as residual acid or acids that may be inhibitory to efficient fermentation).

According to an exemplary embodiment shown in FIG. 5A, after pre-treatment and separation the C5 stream and the C6 stream can be treated separately and subsequently combined after treatment (e.g. as a slurry) for co-fermentation in the fermentation system to produce a C5/C6 fermentation product from the available sugars (e.g. xylose and glucose); the C5/C6 fermentation product can (after treatment, if any) be supplied to the distillation system for recovery of the ethanol (e.g. through distillation and dehydration). According to an exemplary embodiment shown in FIG. 5B, the C5 stream and the C6 stream can each be separately processed through fermentation and distillation (after treatment, if any) to produce ethanol. According to any preferred embodiment, a suitable fermenting organism (ethanologen) will be used in the fermentation system; the selection of an ethanologen may be based on various considerations, such as the predominant types of sugars present in the slurry. Dehydration and/or denaturing of the ethanol produced from the C5 stream and the C6 stream may be performed either separately or in combination.

Figure 6A:
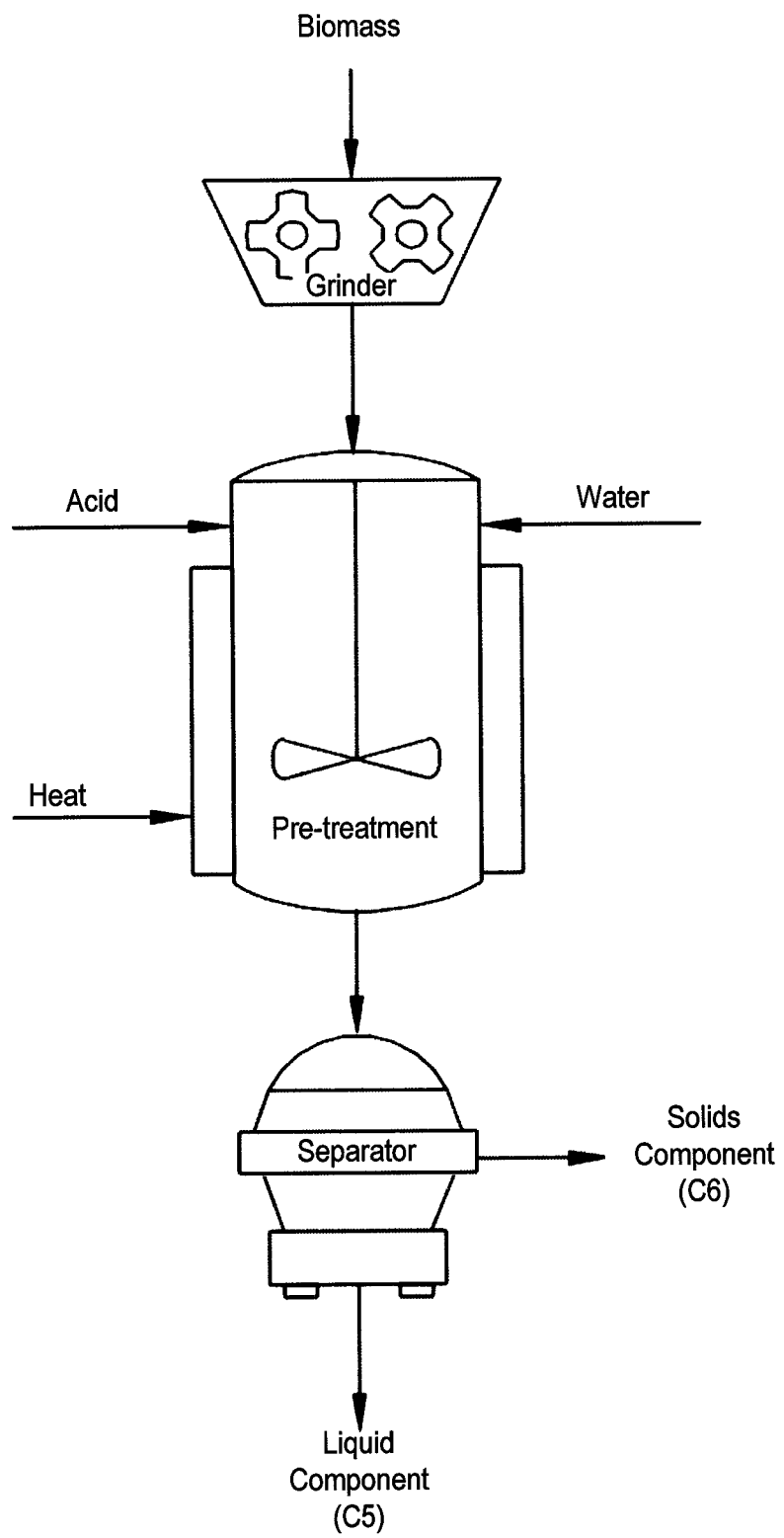
FIG. 6A is a schematic block diagram of apparatus used for preparation, pre-treatment and separation of biomass.
Figure 6B:
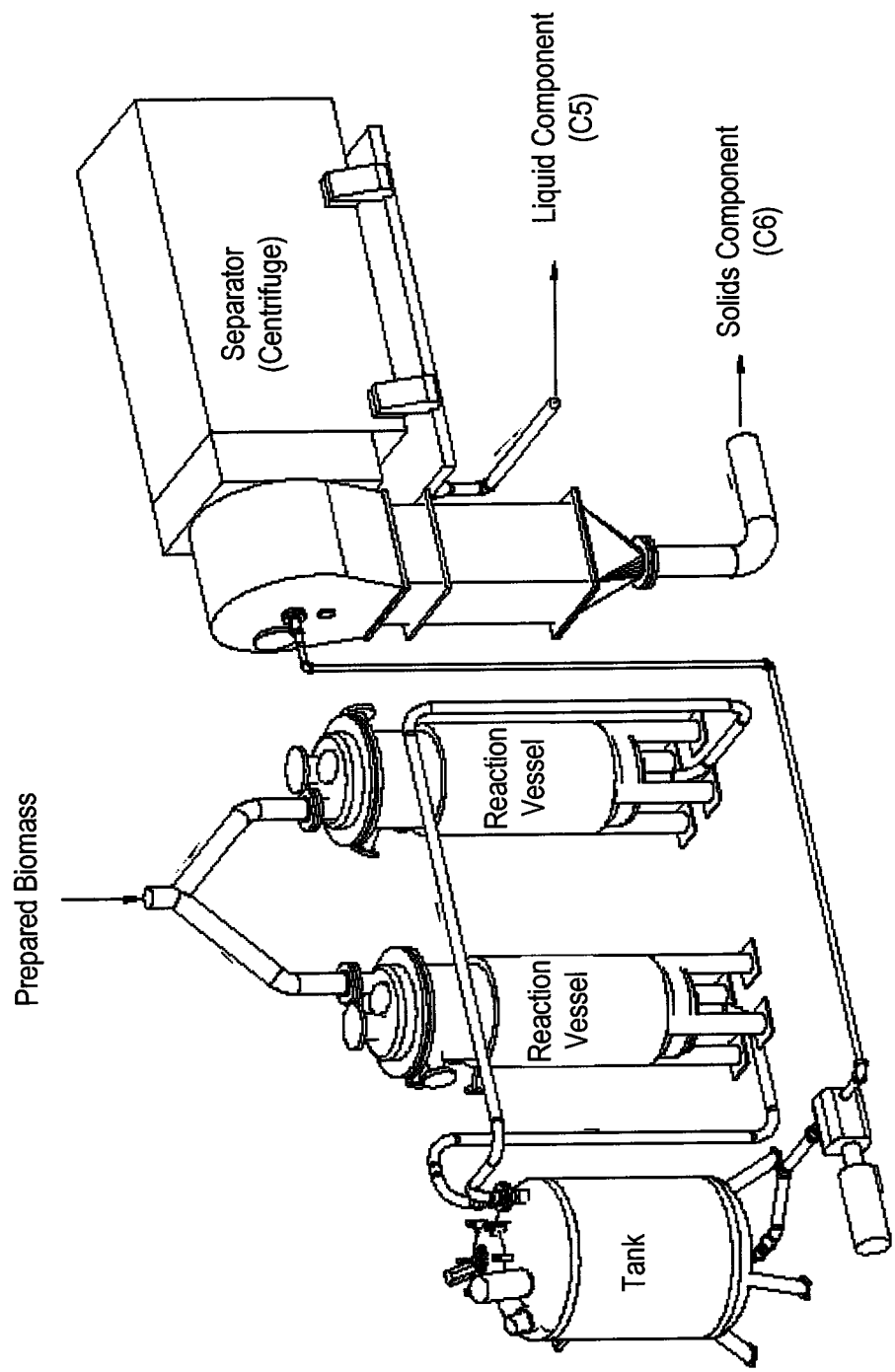
FIG. 6B is a perspective view of apparatus used to pre-treat and separate the biomass.

FIGS. 6A and 6B show the apparatus used for preparation, pre-treatment and separation of lignocellulosic biomass according to an exemplary embodiment. As shown, biomass is prepared in a grinder (e.g. grinder or other suitable apparatus or mill). Pre-treatment of the prepared biomass is performed in a reaction vessel (or set of reaction vessels) supplied with prepared biomass and acid/water in a predetermined concentration (or pH) and other operating conditions. As shown in FIG. 6B, the pre-treated biomass can be separated in a centrifuge into a liquid component (C5 stream comprising primarily liquids with some solids) and a solids component (C6 stream comprising liquids and solids such as lignin and cellulose from which glucose can be made available by further treatment).

Figure 7A:
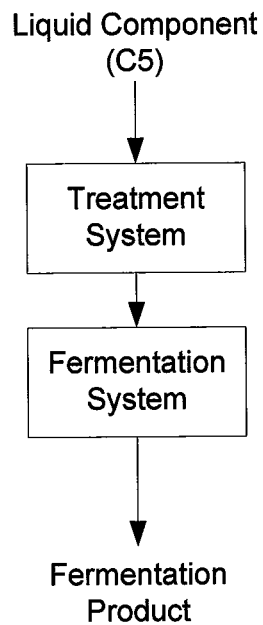
FIGS. 7A and 7B are schematic block diagrams of a treatment system and fermentation system according to an exemplary embodiment.
Figure 7B:
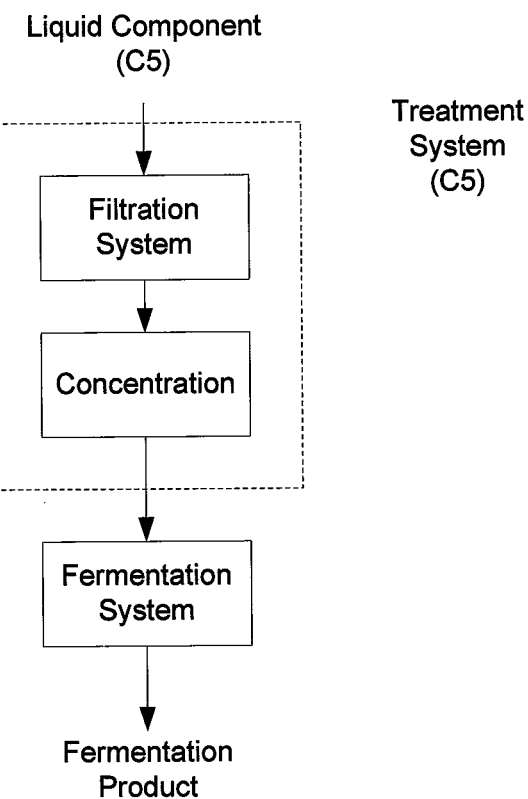
Figure 8A:
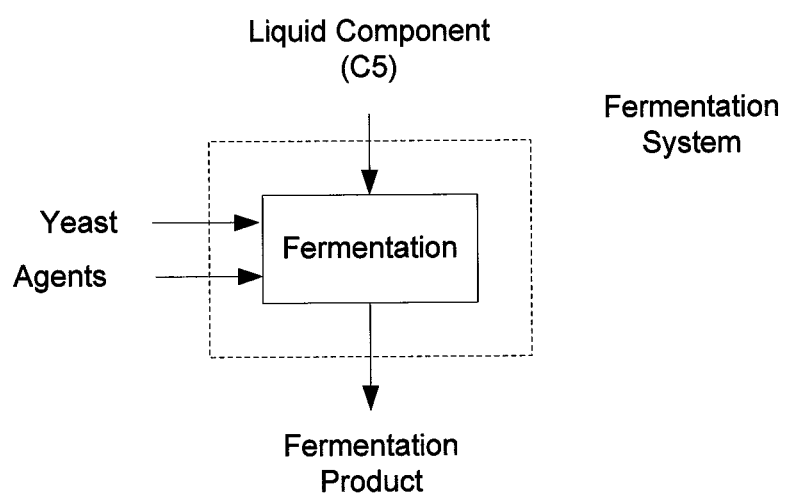
FIG. 8A is a schematic block diagram of a system according to an exemplary embodiment.

Referring to FIGS. 7A and 7B, a treatment system and fermentation system for the liquid component (C5 stream or hydrolysate) of the pre-treated biomass is shown. As shown in FIG. 7B, according to an exemplary embodiment, the treatment system can comprise filtration of the C5 stream to remove inhibitors (such as furfural and acetic acid) and concentration of the C5 stream to facilitate the efficient fermentation of sugars (e.g. xylose and glucose). As shown in FIG. 8A, according to an exemplary embodiment, the fermentation system can comprise the fermentation of the C5 stream by the application of an ethanologen (i.e. an organism shown as yeast cells) and agents (such as nutrients) for the ethanologen to yield a fermentation product.

According to an exemplary embodiment, the fermentation product is produced in the fermentation system by application of the ethanologen to convert the sugars in the C5 stream (hydrolysate of the pre-treated biomass) into ethanol. According to a preferred embodiment, the ethanologen for the fermentation system may comprise an organism (i.e. yeast) selected for efficient fermentation of the xylose and glucose that is present in the C5 stream. According to a particularly preferred embodiment, the ethanologen for the C5 stream may be a genetically modified organism as described in U.S. Pat. No. 7,622,284, assigned to Royal Nedalco B.V. According to an alternative embodiment, the ethanologen may comprise a formulation or combination of organisms (e.g. one type of yeast selected for fermentation of C5 sugars such as xylose and one type of yeast selected for fermentation of C6 sugars such as glucose). According to exemplary embodiments, the amount or loading (dose) of ethanologen (i.e. yeast cells) may be varied in the operation of the fermentation system. Agents supplied with the ethanologen may include antibiotics, supplemental or accessory enzymes, urea, salts (such as zinc or magnesium salts), or other component providing nutritional or other benefit to the organism.

Figure 9A:
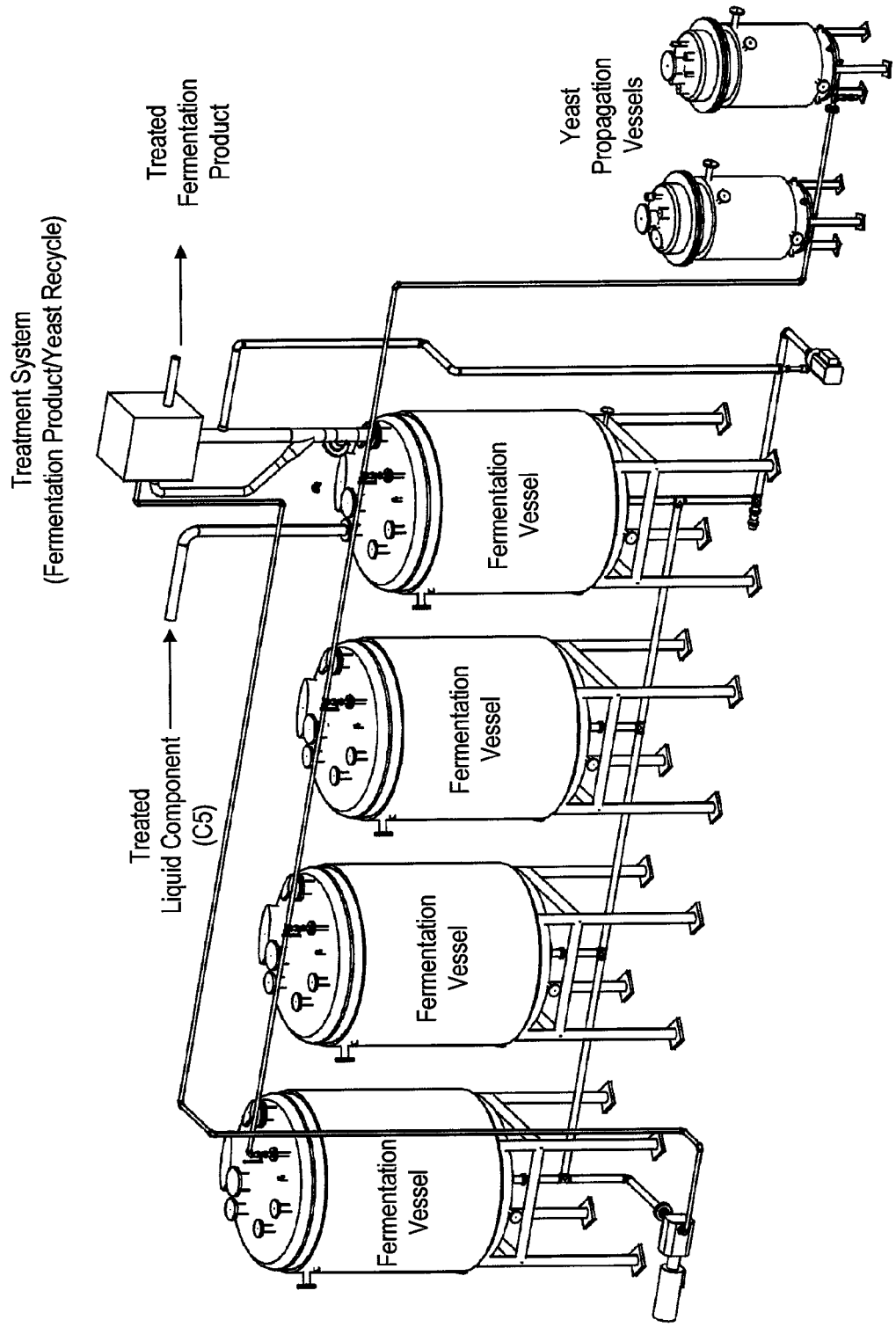
FIGS. 9A and 9B are perspective view of fermentation system according to exemplary embodiments.
Figure 9B:
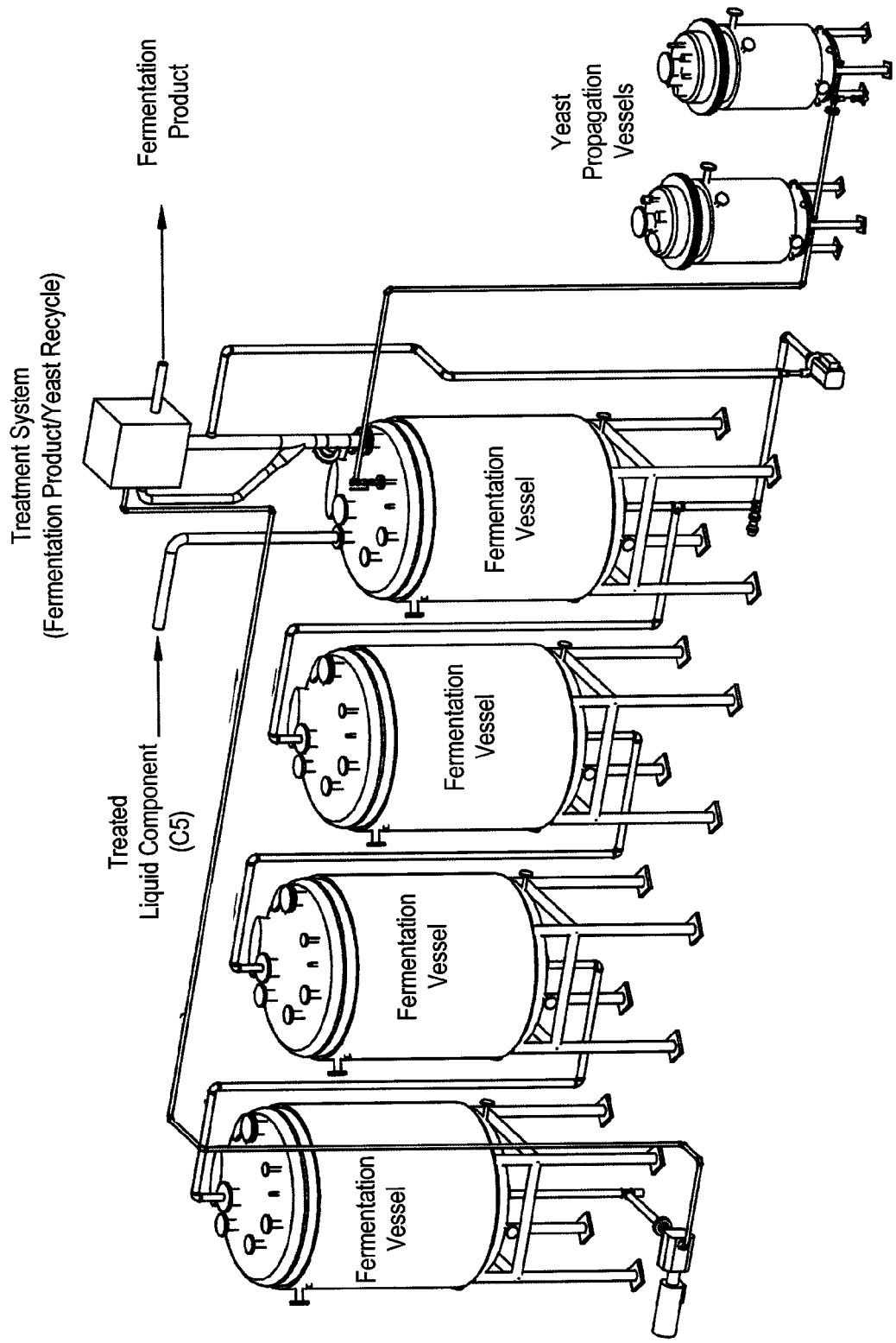

Referring to FIGS. 9A and 9B, the fermentation system may operate in a batch, fed batch, continuous flow, or other arrangement. According to an exemplary embodiment, the fermentation system will comprise at least one fermentation tank. According to the exemplary embodiment shown in FIG. 9A, the fermentation system comprises a set of tanks into which the treated C5 stream (i.e. treated hydrolysate from pre-treated biomass, in a slurry) is supplied, along with the ethanologen and nutrients (as needed). As shown in FIGS. 9A and 9B, ethanologen (shown as yeast) is supplied from a yeast propagation system comprising a tank (maintained under operating conditions suitable for growth of a suitable quantity of yeast/organism from seed or source). Fermentation is conducted under operating conditions selected to facilitate the efficient conversion of the sugars in the C5 stream/hydrolysate into ethanol. Operating conditions for the fermentation system will comprise time, temperature, pH, solids loading and ethanologen loading.

According to an exemplary embodiment using batch fermentation, as shown in FIG. 9A, the fermentation system comprises multiple tanks and is configured so that fermentation can be conducted simultaneously in multiple fermentation tanks. The slurry (treated hydrolysate/C5 stream), ethanologen and nutrients will be supplied to each of the fermentation tanks according to a sequence. Fermentation will be performed for a designated period of time under the designated operating conditions for each particular tank; after fermentation has been completed in the particular tank, the tank will then be emptied of fermentation product and cleaned. According to a preferred embodiment, one tank will be available to receive and be filled with slurry as it is produced; fermentation will be taking place in at least one other tank; and another tank in which fermentation has been completed may be being emptied and readied to be filled and used for another fermentation. The operating conditions for fermentation (as well as samples of the slurry being fermented) may be monitored and controlled in each fermentation tank.

According to an exemplary embodiment using continuous fermentation, as shown in FIG. 9B, the fermentation system comprises multiple tanks in a cascade arrangement. The fermentation system is configured so that the slurry (treated hydrolysate/C5 stream) and ethanologen/nutrients are initially supplied to a first tank. As fermentation proceeds in the tank, partially-fermented slurry in the process of being fermented is flowed into the next tank in sequence; when emptied from the final tank, the slurry has been completely fermented into fermentation product. The operating conditions for fermentation (as well as samples of the slurry being fermented) may be monitored and controlled in each fermentation tank.

The fermentation product (which may also be referred to as beer or fermentation broth, or as comprising beer or fermentation broth) will comprise ethanol and water, as well as unfermented matter (e.g. any unfermented sugars) and non-fermentable matter (e.g. residual lignin and other solids). The fermentation product will also comprise in the form of particulate matter the ethanologen (i.e. yeast cells) that was used to produce ethanol, as well as other components produced by the fermentation system, for example, such as glycerol (a product of fermentation) and acetic acid.

Figure 8B:
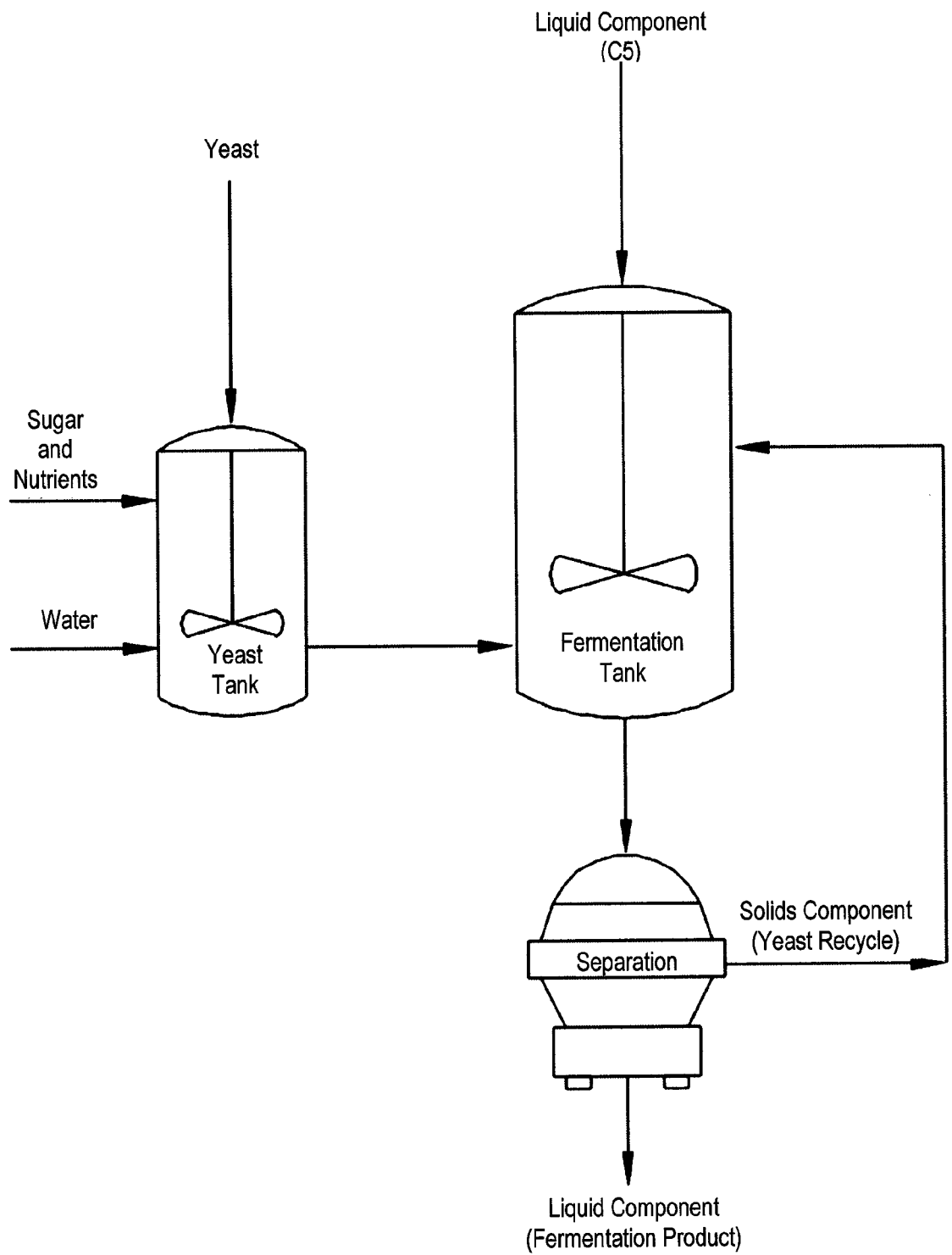
FIG. 8B is a schematic block diagram of a fermentation system and treatment system according to an exemplary embodiment.

As shown in FIG. 8B, according to an exemplary embodiment, a treatment system for the fermentation product may also be provided. The treatment system can comprise separation of the fermentation product into a liquid component (i.e. a treated fermentation product, which will comprise substantially ethanol and water) and a solids component (which will comprise substantially solids matter such as the ethanologen/yeast cells). According to a preferred embodiment, as shown in FIG. 8B, the separation of the fermentation product into the liquid component and solids component can be performed on a centrifuge; according to other exemplary embodiments, the separation may be performed in other apparatus (or other equipment configured to separate solids and liquids). As shown in FIG. 8B, the solids component from treatment comprising the yeast cells can be supplied to and re-used in the fermentation system (i.e. recycled for use in a fermentation tank) along with additional or fresh yeast cells (if necessary).

As shown in FIGS. 2, 5A and 5B, the liquid component (or treated fermentation product) from the treatment system can be supplied to the distillation system, for distillation and dehydration to allow recovery of ethanol.

FIGS. 10A through 10D show operating conditions for subject parameters of the fermentation system according to an exemplary embodiment of the system (configured for the fermentation of the treated liquid component/C5 stream of biomass in the form of corn cobs and stover, following acid pre-treatment and separation); operating conditions are shown in the form of nested ranges comprising an acceptable operating range (the outer/wide range shown), a preferred operating range (the middle range shown), and a particularly preferred operating range (the inner/narrow range shown) for each subject condition or parameter.

Figure 10A:
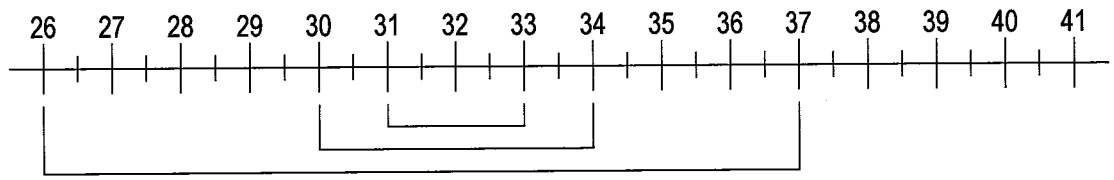
FIGS. 10A through 10D are diagrams of operating conditions for the fermentation system according to an exemplary embodiment.

FIG. 10A shows the temperature ranges for operation of a fermentation system according to exemplary embodiments. According to an exemplary embodiment, the operating temperature range is about to about 37 degrees Celsius. According to a preferred embodiment, the operating temperature is from about 30 to about 34 degrees Celsius. According to a particularly preferred embodiment, the operating temperature is from about 31 to about 34 degrees Celsius.

Figure 10B:
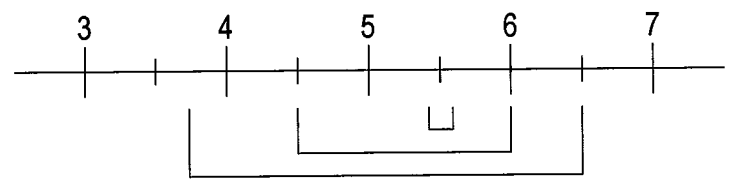

FIG. 10B shows the pH ranges for operation of a fermentation system according to exemplary embodiments. According to an exemplary embodiment, the pH range is about 3.7 to about 6.5. According to a preferred embodiment, the pH is from about 4.5 to about 6.0. According to a particularly preferred embodiment, the pH is from about 5.4 to about 5.6.

Figure 10C:
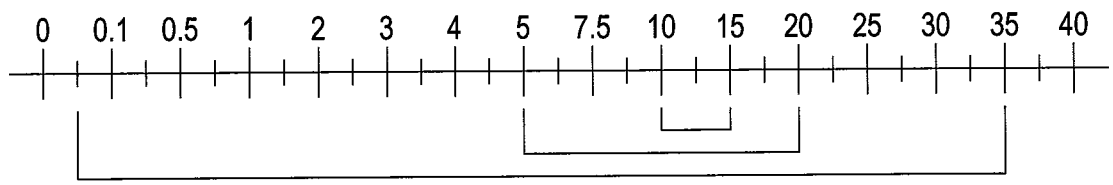

FIG. 10C shows the yeast loading (in grams of dry yeast per liter of hydrolysate) for operation of a fermentation system according to exemplary embodiments (for example, a genetically modified yeast derived from the organism disclosed in U.S. Pat. No. 7,622,284, incorporated by reference, assigned to Royal Nedalco, B.V.). According to an exemplary embodiment, the yeast loading is about 0.05 to about 35 grams per liter. According to a preferred embodiment, the yeast loading is from about 5 to about 20 grams per liter. According to a particularly preferred embodiment, the yeast loading is from about 10 to about 15 grams per liter.

Figure 10D:
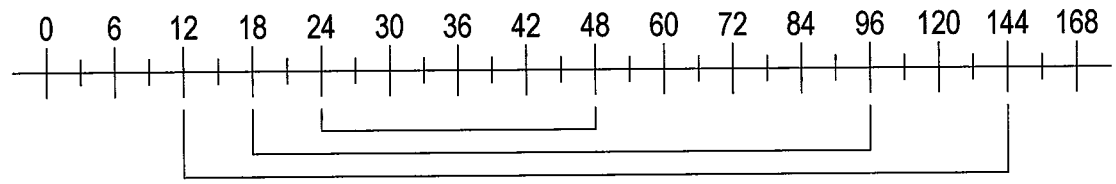

FIG. 10D shows the time for operation of a batch fermentation system according to exemplary embodiments (excluding of time to fill and empty the fermentation tank). According to an exemplary embodiment, the fermentation time is about 12 to 144 hours. According to a preferred embodiment, the fermentation time is about 18 to 96 hours. According to a particularly preferred embodiment, the fermentation time is about 24 to 48 hours.

According to other alternative embodiments, for example, using a different form or type of biomass or a different ethanologen, the operating conditions for the fermentation system may be varied as necessary to achieve efficient fermentation.

A series of examples were conducted according to an exemplary embodiment of the fermentation system (as shown in FIGS. 11 through 14) in an effort to evaluate efficacy for fermentation of sugars from the C5 stream (e.g. liquid component from separation of pre-treated biomass). The ethanologen used in the examples was a strain of *Saccharomyces cerevisiae* yeast altered to convert xylose and glucose to ethanol (a genetically modified yeast derived from an organism as described in U.S. Pat. No. 7,622,284 by Royal Nedalco B.V., for example strain No. RWB218 and strain No. RN1001). Data from the examples is shown in TABLES 4 through 7. The biomass comprised corn cobs and stover.

Example 1

Figure 11:
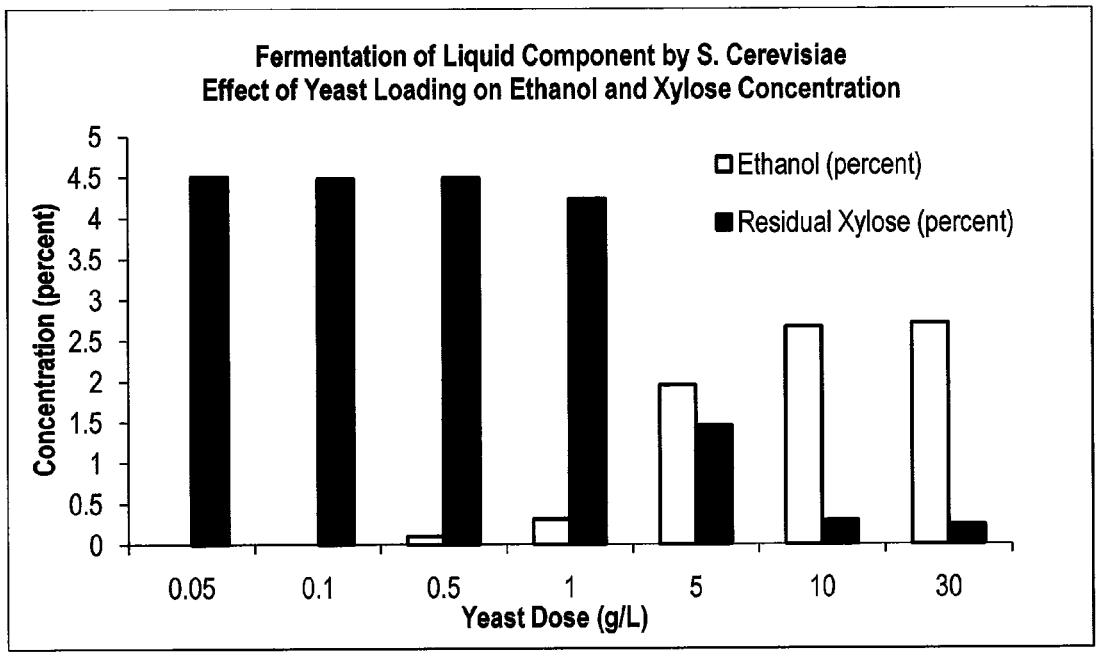
FIG. 11 is a graph of results obtained through the use of the fermentation system according to an exemplary embodiment.

The fermentation system was used in Example 1 to evaluate the effect of ethanologen loading on the efficacy of the ethanologen in the fermentation of xylose into ethanol, as indicated in FIG. 11. The ethanologen was yeast (strain No. RWB218.) A sample was prepared having an initial xylose concentration of about 4.7 percent (by weight). The sample was divided into subsamples, which were supplied with a yeast loading between about 0.05 and 30 grams per liter (of sample) in a fermentation system to produce a fermentation product. The fermentation was conducted at approximately 32 degrees Celsius and approximately pH 5.5 for approximately 48 hours. The subsamples were analyzed for xylose concentration and ethanol concentration. It was observed that at least about 5 grams per liter of yeast was needed for sufficient fermentation of xylose to ethanol under the operating conditions. The results are shown in FIG. 11 and TABLE 4.

Example 2A

Figure 12A:
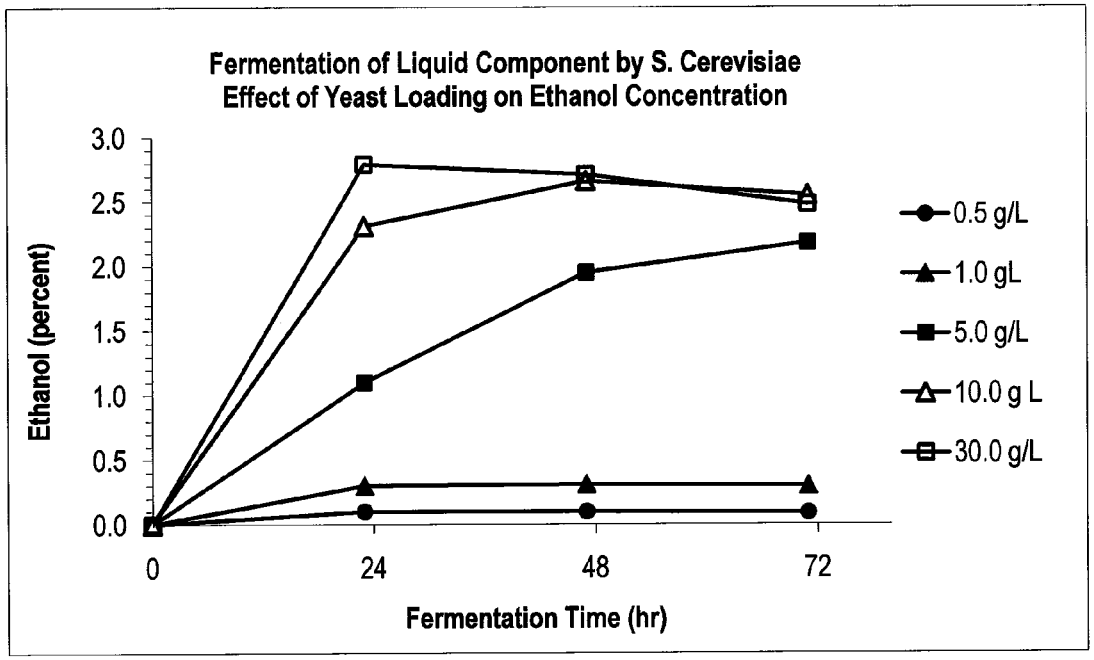
FIGS. 12A and 12B are a graph of results obtained through the use of the fermentation system according to an exemplary embodiment.
Figure 12B:
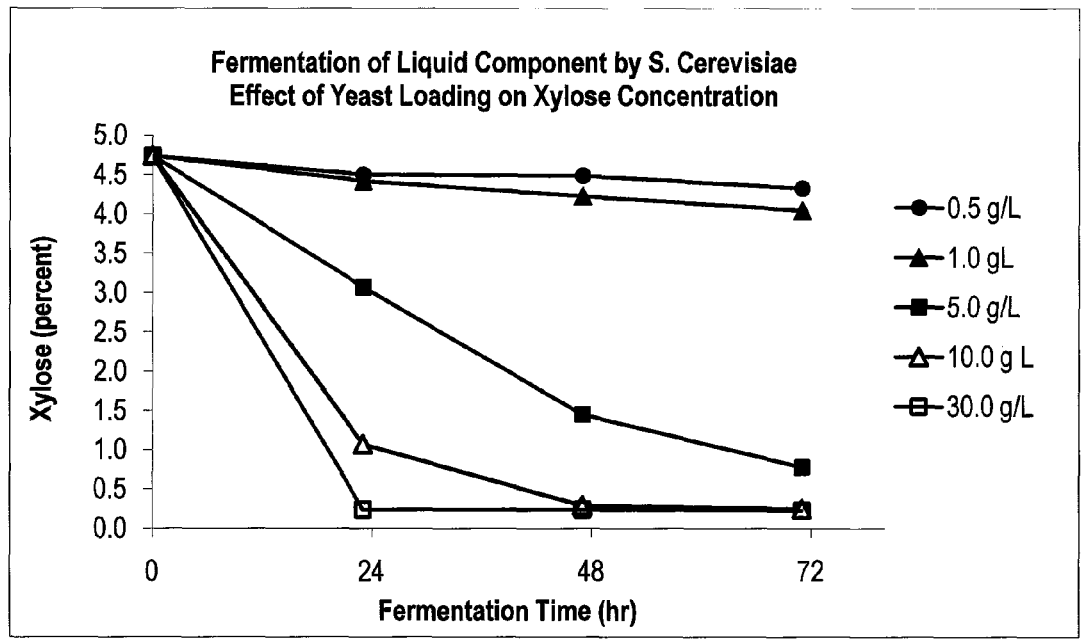

The fermentation system was used in Example 2A to evaluate the efficacy of the ethanologen in the fermentation of xylose in a hydrolysate from the liquid component (i.e. C5 stream) of pre-treated biomass at varying levels of initial loading (i.e. yeast concentration), as indicated in FIGS. 12A and 12B. The ethanologen was yeast (strain No. RWB218.) A sample of the hydrolysate was prepared including about 4.7 percent xylose (by weight). The sample was divided into subsamples, which were supplied with a yeast loading between about 0.5 and 30 grams per liter (of sample) in a fermentation system to produce a fermentation product. The fermentation was conducted at approximately 32 degrees Celsius and approximately pH 5.5 for approximately 72 hours. The subsamples were analyzed for xylose concentration and ethanol concentration at 24 hours, 48 hours and about 72 hours (the end of fermentation). It was observed that at least about 5 grams per liter of yeast was needed for sufficient fermentation of xylose to ethanol and that efficient fermentation could be achieved at about 10 grams per liter under the operating conditions. The results are shown in FIGS. 12A and 12B and TABLES 5A and 5B.

Example 2B

Figure 13A:
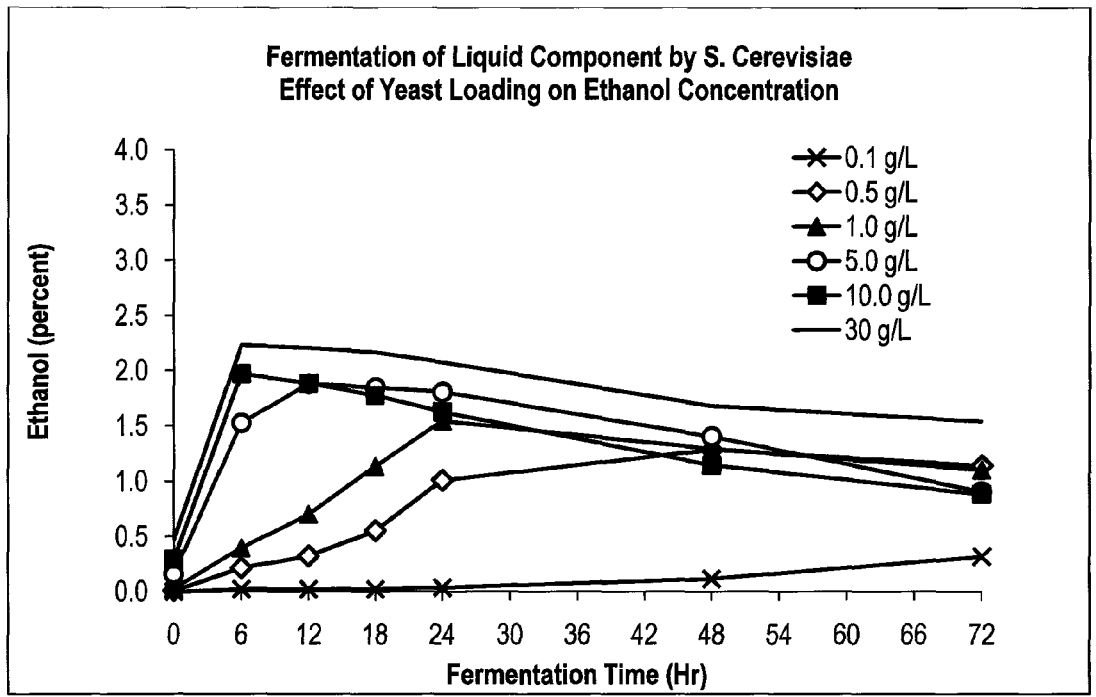
FIGS. 13A and 13B are a graph of results obtained through the use of the fermentation system according to an exemplary embodiment.
Figure 13B:
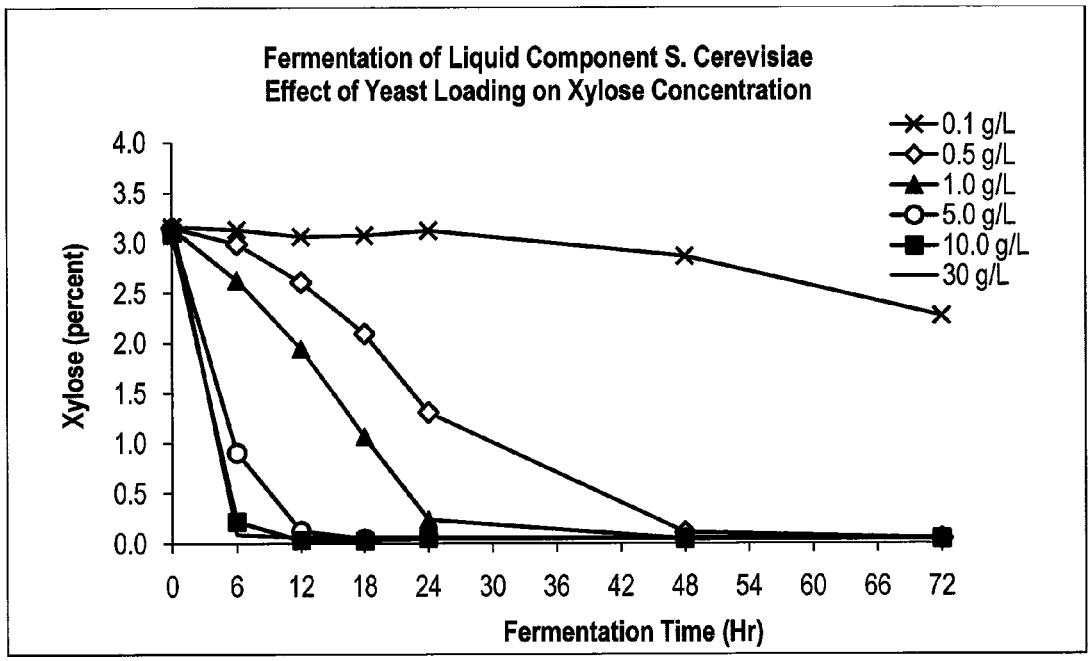

The fermentation system was used in Example 2B to evaluate the efficacy of the ethanologen in the fermentation of xylose in a hydrolysate from the liquid component (i.e. C5 stream) of pre-treated biomass at varying levels of initial loading (i.e. yeast concentration), as indicated in FIGS. 13A and 13B. The ethanologen was yeast (strain No. RN1001.) A sample of the hydrolysate was prepared comprising about 3.1 to 3.2 percent xylose (by weight) and less than 3800 PPM of acetic acid. The sample was divided into subsamples, which were supplied with a yeast loading between about 0.1 and 30 grams per liter (of sample) in a fermentation system to produce a fermentation product. The fermentation was conducted at approximately 32 degrees Celsius and approximately pH 5.5 for approximately 72 hours. The subsamples were analyzed for xylose concentration and ethanol concentration at 6 hours, 12 hours, 18 hours, 24 hours, 48 hours and about 72 hours (the end of fermentation). It was observed that at least about 1 gram per liter of yeast was needed for sufficient fermentation of xylose to ethanol under the operating conditions. The results are shown in FIGS. 13A and 13B and TABLE 6.

Example 3

Figure 14:
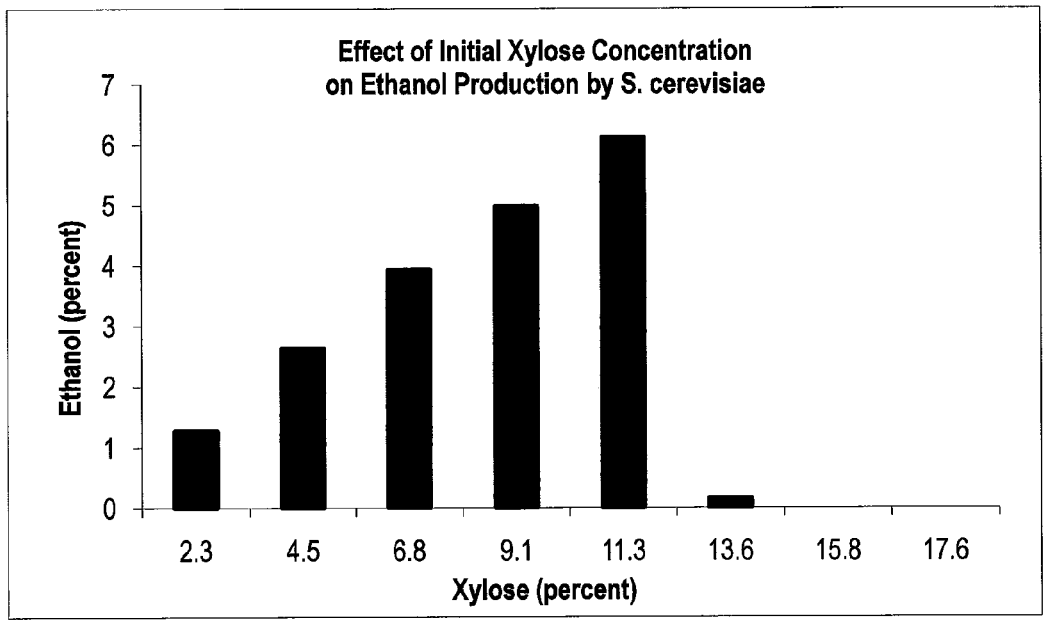
FIG. 14 is a graph of results obtained through the use of the fermentation system according to an exemplary embodiment.

The fermentation system was used in Example 3 to evaluate the effect of xylose concentration on the efficacy (and xylose tolerance) of the ethanologen in the fermentation of xylose into ethanol, as indicated in FIG. 14. The ethanologen was yeast (strain No. RWB218.) A sample was prepared using a sterile medium comprising 1 gram per liter (of sample) yeast extract and 1 gram per liter (of sample) soy peptone and an initial yeast loading (inoculation rate) of about 0.59 grams per liter (of sample). The sample was divided into subsamples and supplied to a fermentation system to produce a fermentation product; subsamples were fermented with initial xylose concentrations between about 2.3 percent and 17.6 percent (by weight). The fermentation was conducted at approximately 32 degrees Celsius and approximately pH 5.5 for approximately 72 hours. The subsamples were analyzed for xylose concentration and ethanol concentration at 72 hours (the end of fermentation). It was observed that the yeast was able to convert xylose to ethanol at a xylose concentration at and below approximately 11.3 percent (by weight), but was no longer efficient at a xylose concentration at or above approximately 13.6 percent (by weight) under the operating conditions. The results are shown in FIG. 14 and TABLE 7.

The embodiments as disclosed and described in the application (including the FIGURES and Examples) are intended to be illustrative and explanatory of the present inventions. Modifications and variations of the disclosed embodiments, for example, of the apparatus and processes employed (or to be employed) as well as of the compositions and treatments used (or to be used), are possible; all such modifications and variations are intended to be within the scope of the present inventions.

TABLE 1A

Biomass Composition

| Cob (percent) | Husks/Leaves (percent) | Stalk (percent) | Cellulose (Glucan) (percent) | Hemicellulose Xylan (percent) | Arabinan (percent) | Acetate (percent) | Composite (percent) | Lignin (percent) | Ash (percent) |
|---|---|---|---|---|---|---|---|---|---|
| 100 | 0 | 0 | 36.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |
| 0 | 0 | 100 | 41.7 | 22.5 | 2.4 | 2.6 | 27.5 | 18.3 | 3.7 |
| 50 | 0 | 50 | 38.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 30 | 50 | 20 | 37.7 | 27.3 | 4.0 | 2.5 | 33.8 | 14.6 | 5.3 |

TABLE 1B

Biomass Typical and Expected Composition

| | Cellulose (Glucan) (percent) (approx.) | Hemicellulose (percent) (approx.) | Lignin (percent) (approx.) | Ash (percent) (approx.) |
|---|---|---|---|---|
| Typical Range | 35-45 | 24-42 | 12-20 | 2-8 |
| Expected Range | 30-55 | 20-50 | 10-25 | 1-10 |

TABLE 2A

Pre-Treated Biomass Liquid Component Composition

| Cob (percent) | Husks/Leaves (percent) | Stalk (percent) | Glucose (percent) | Xylose (percent) | Arabinose (percent) | Acetic Acid (PPM) |
|---|---|---|---|---|---|---|
| 100 | 0 | 0 | 0.4 | 4.8 | 0.5 | 6090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6135 |
| 30 | 50 | 20 | 0.4 | 3.6 | 0.5 | 4763 |

TABLE 2B

Pre-Treated Biomass Liquid Component Typical and Expected Composition

| | Glucose (percent) (approx.) | Xylose (percent) (approx.) | Arabinose (percent) (approx.) | Acetic Acid (PPM) (approx.) |
|---|---|---|---|---|
| Typical Range | 0-1 | 2-6 | 0-1 | 3000-6400 |
| Expected Range | 0-1 | 1-8 | 0-1 | 2000-8000 |

TABLE 3A

Pre-Treated Biomass
Solids Component Composition

| Husks/ | | | Cellulose | Hemicellulose | | | | Lignin | Ash |
|---|---|---|---|---|---|---|---|---|---|
| Cob (percent) | Leaves (percent) | Stalk (percent) | (Glucan) (percent) | Xylan (percent) | Arabinan (percent) | Acetate (percent) | Composite (percent) | (percent) | (percent) |
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 3.1 |
| 50 | 0 | 50 | 55.7 | 5.5 | 0.9 | 0.6 | 13.1 | 27.0 | 2.2 |
| 50 | 50 | 0 | 57.3 | 5.4 | 0.8 | 0.5 | 10.6 | 25.2 | 5.4 |
| 30 | 50 | 20 | 55.5 | 3.8 | 0.8 | 0.6 | 11.5 | 25.4 | 5.8 |

TABLE 3B

Pre-Treated Biomass
Solids Component
Typical and Expected Composition

| | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 5-20 | 20-32 | 1-10 |

TABLE 4

| Yeast Loading (g/L*) | Ethanol (percent) | Residual Xylose (percent) |
|---|---|---|
| 0.05 | 0.00 | 4.50 |
| 0.1 | 0.00 | 4.48 |
| 0.5 | 0.10 | 4.49 |
| 1 | 0.31 | 4.23 |
| 5 | 1.95 | 1.45 |
| 10 | 2.66 | 0.29 |
| 30 | 2.71 | 0.24 |

*grams per Liter of medium

TABLE 5A

| | Ethanol (percent) | | | | |
|---|---|---|---|---|---|
| Time (h) | 0.5 g/L | 1.0 g/L | 5.0 g/L | 10.0 g/L | 30.0 g/L |
| 0 | 0.00 | 0.00 | 0.00 | 0.00 | 0.00 |
| 23 | 0.10 | 0.30 | 1.10 | 2.31 | 2.79 |
| 47 | 0.10 | 0.31 | 1.95 | 2.66 | 2.71 |
| 71 | 0.09 | 0.30 | 2.18 | 2.55 | 2.48 |

TABLE 5B

| | Residual xylose (percent) | | | | |
|---|---|---|---|---|---|
| Time (h) | 0.5 g/L | 1.0 g/L | 5.0 g/L | 10.0 g/L | 30.0 g/L |
| 0 | 4.74 | 4.74 | 4.74 | 4.74 | 4.74 |
| 23 | 4.50 | 4.42 | 3.07 | 1.07 | 0.24 |
| 47 | 4.49 | 4.23 | 1.45 | 0.29 | 0.24 |
| 71 | 4.33 | 4.05 | 0.78 | 0.25 | 0.23 |

TABLE 6

| Yeast Cell Loading 0.1 g/L | | | | | Yeast Cell Loading 0.5 g/L | | | | |
|---|---|---|---|---|---|---|---|---|---|
| Time (hr) | Ethanol (percent) | Xylose (percent) | Glucose (percent) | Acetic Acid (PPM) | Time (hr) | Ethanol (percent) | Xylose (percent) | Glucose (percent) | Acetic Acid (PPM) |
| 0 | 0.00 | 3.16 | 0.25 | 3628 | 0 | 0.01 | 3.16 | 0.24 | 3619 |
| 6 | 0.02 | 3.13 | 0.20 | 3647 | 6 | 0.22 | 2.99 | 0.04 | 3625 |
| 12 | 0.02 | 3.06 | 0.19 | 3632 | 12 | 0.32 | 2.61 | 0.00 | 3554 |
| 18 | 0.02 | 3.07 | 0.18 | 3610 | 18 | 0.55 | 2.09 | 0.00 | 3440 |
| 24 | 0.04 | 3.12 | 0.17 | 3682 | 24 | 1.01 | 1.31 | 0.00 | 3364 |
| 48 | 0.12 | 2.87 | 0.05 | 3394 | 48 | 1.29 | 0.11 | 0.03 | 2612 |
| 72 | 0.32 | 2.27 | 0.02 | 2869 | 72 | 1.14 | 0.05 | 0.03 | 2097 |

| Yeast Cell Loading 1.0 g/L | | | | | Yeast Cell Loading 5.0 g/L | | | | |
|---|---|---|---|---|---|---|---|---|---|
| Time (hr) | Ethanol (percent) | Xylose (percent) | Glucose (percent) | Acetic Acid (PPM) | Time (hr) | Ethanol (percent) | Xylose (percent) | Glucose (percent) | Acetic Acid (PPM) |
| 0 | 0.03 | 3.15 | 0.23 | 3621 | 0 | 0.16 | 3.13 | 0.11 | 3689 |
| 6 | 0.40 | 2.63 | 0.00 | 3635 | 6 | 1.53 | 0.91 | 0.00 | 3939 |
| 12 | 0.70 | 1.94 | 0.00 | 3630 | 12 | 1.88 | 0.13 | 0.00 | 4073 |
| 18 | 1.14 | 1.07 | 0.00 | 3566 | 18 | 1.85 | 0.05 | 0.00 | 4201 |
| 24 | 1.55 | 0.24 | 0.02 | 3532 | 24 | 1.81 | 0.06 | 0.00 | 4560 |
| 48 | 1.30 | 0.05 | 0.03 | 3193 | 48 | 1.41 | 0.05 | 0.04 | 6232 |
| 72 | 1.11 | 0.04 | 0.04 | 2532 | 72 | 0.91 | 0.05 | 0.04 | 8382 |

TABLE 6-continued

| Yeast Cell Loading 10 g/L | | | | | Yeast Cell Loading 30 g/L | | | | |
|---|---|---|---|---|---|---|---|---|---|
| Time (hr) | Ethanol (percent) | Xylose (percent) | Glucose (percent) | Acetic Acid (PPM) | Time (hr) | Ethanol (percent) | Xylose (percent) | Glucose (percent) | Acetic Acid (PPM) |
| 0 | 0.29 | 3.10 | 0.04 | 3691 | 0 | 0.47 | 3.23 | 0.00 | 3782 |
| 6 | 1.97 | 0.22 | 0.00 | 4094 | 6 | 2.23 | 0.09 | 0.04 | 4218 |
| 12 | 1.89 | 0.03 | 0.00 | 4447 | 12 | 2.21 | 0.06 | 0.07 | 4984 |
| 18 | 1.78 | 0.03 | 0.01 | 4703 | 18 | 2.17 | 0.06 | 0.08 | 5369 |
| 24 | 1.63 | 0.05 | 0.04 | 5045 | 24 | 2.08 | 0.06 | 0.07 | 5740 |
| 48 | 1.15 | 0.05 | 0.06 | 6440 | 48 | 1.68 | 0.06 | 0.09 | 7255 |
| 72 | 0.89 | 0.05 | 0.06 | 7563 | 72 | 1.54 | 0.05 | 0.09 | 9061 |

TABLE 7

| Xylose (%) | Ethanol (%) |
|---|---|
| 2.30 | 1.28 |
| 4.53 | 2.64 |
| 6.76 | 3.93 |
| 9.06 | 4.98 |
| 11.30 | 6.12 |
| 13.60 | 0.16 |
| 15.80 | 0.00 |
| 17.60 | 0.00 |

We claim:

1. A method for producing a fermentation product in a fermentation system from a biomass comprising the steps of:
   (i) pre-treating the biomass with an aqueous composition comprising an effective concentration of acid for reducing formation of inhibitors at a temperature of about 130° C. to about 170° C. for a period of time sufficient to produce a solids component and an aqueous component, which aqueous component comprises xylose and acetic acid;
   (ii) supplying the aqueous component to the fermentation system;
   (iii) providing yeast to the fermentation system in a concentration in the range from 5 to less than 150 grams of yeast on a dry basis per liter of the aqueous component, wherein the yeast can ferment the xylose into the fermentation product;
   (iv) maintaining the aqueous component and yeast in the fermentation system at a temperature of between about 26° C. and about 37° C. and at a pH of between about 4.5 and about 6.0 for a time of no less than 18 hours; and
   (v) recovering the fermentation product from the fermentation system;
   wherein the biomass comprises lignocellulosic material.

2. The method of claim 1, wherein the lignocellulosic material consists essentially of corn cobs, corn plant husks, corn plant leaves and corn stalks.

3. The method of claim 1, wherein the aqueous component comprises xylose at about 2 to 5 percent by weight.

4. The method of claim 1, wherein the aqueous component further comprises glucose and the yeast is capable of fermenting both the xylose and glucose into ethanol.

5. The method of claim 1, wherein the yeast comprises *Saccharomyces cerevisiae*.

6. The method of claim 1, wherein the fermentation product comprises at least 1.5 percent ethanol by volume.

7. The method of claim 1, wherein the fermentation product comprises at least 2.0 percent ethanol by volume.

8. The method of claim 1, wherein the fermentation product comprises ethanol and wherein at least 75 percent of the xylose has been converted into ethanol by fermentation.

9. The method of claim 1, further comprising the step of treating the aqueous component to increase the concentration of xylose.

10. The method of claim 1, wherein the lignocellulosic-material comprises cellulose and lignin.

11. The method of claim 1, wherein the step of maintaining the aqueous component and yeast in the fermentation system is for a time of no less than 24 hours.

12. The method of claim 1, wherein the lignocellulosic material comprises at least one of corn cobs, corn plant husks, corn plant leaves and corn plant stalks.

13. The method of claim 1, further comprising the step of
   (vii) supplying the solids component to the fermentation system;
   wherein the solids component comprises hexose.

14. The method of claim 1, wherein the acid concentration is between about 0.8 and 1.1 percent by weight.

15. The method of claim 1, wherein the acid concentration is between about 0.05 and 0.5 percent by weight.

16. The method of claim 1, wherein the acetic acid is present in the aqueous component in an amount in the range from 3,000 to 6,400 parts per million.